(12) United States Patent
Cleary et al.

(10) Patent No.: US 8,648,050 B2
(45) Date of Patent: *Feb. 11, 2014

(54) METHODS AND FORMULATIONS FOR REDUCING AMPHOTERICIN B TREATMENT SIDE EFFECTS

(75) Inventors: John D. Cleary, Brandon, MS (US); Stanley W. Chapman, Jackson, MS (US); Robert E. Kramer, Brandon, MS (US)

(73) Assignee: University of Mississippi, University, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/985,256

(22) Filed: Jan. 5, 2011

(65) Prior Publication Data

US 2011/0152211 A1    Jun. 23, 2011

(51) Int. Cl.
*A61K 31/70* (2006.01)
*C07H 17/08* (2006.01)

(52) U.S. Cl.
USPC .............................. 514/31; 536/6.5

(58) Field of Classification Search
USPC ............................. 536/6.5; 514/31
See application file for complete search history.

(56) References Cited

U.S. PATENT DOCUMENTS

| | | |
|---|---|---|
| 3,965,090 A | 6/1976 | Metzger |
| 4,035,568 A | 7/1977 | Schaffner et al. |
| 4,049,898 A | 9/1977 | Metzger |
| 4,054,734 A | 10/1977 | Metzger |
| 4,308,375 A | 12/1981 | Tang |
| 4,656,288 A | 4/1987 | Ono et al. |
| 4,663,167 A | 5/1987 | Lopez-Berestein et al. |
| 4,766,046 A | 8/1988 | Abra et al. |
| 4,902,789 A | 2/1990 | Michel et al. |
| 5,194,266 A | 3/1993 | Abra et al. |
| 5,616,334 A | 4/1997 | Janoff et al. |
| 5,965,156 A | 10/1999 | Proffitt et al. |
| 6,068,839 A * | 5/2000 | Kazutoh et al. ............... 424/116 |
| 6,406,713 B1 | 6/2002 | Janoff et al. |

* cited by examiner

*Primary Examiner* — Elli Peselev
(74) *Attorney, Agent, or Firm* — Stites & Harbison PLLC; Richard S. Myers, Jr.

(57) ABSTRACT

A method of ameliorating amphotericin treatment side effects in a mammal that comprises administering a therapeutically effective amount of a formulation that comprises a polyene active ingredient that includes amphotericin B, wherein the amphotericin B compound is present, in terms of polyene content, in an amount greater than 90%, and non-amphotericin B polyene compounds are present in an amount of no greater than 10%, and a pharmaceutically effective carrier; and administering a therapeutically effective amount of said formulation to a subject in need thereof.

30 Claims, 17 Drawing Sheets

Survival Studies In Disseminated Candidiasis

The clear rectangle indicates the portion of column effluent that was collected as AmBHP.

METHODS AND FORMULATIONS FOR REDUCING AMPHOTERICIN B TREATMENT SIDE EFFECTS

GOVERNMENT SUPPORT

This invention was made with support from NIH/NIAID Grant No. R41 AI63935-01A1. The government has certain rights to this invention.

PRIORITY

This application claims priority to U.S. patent application Ser. No. 10/529,622, now issued as U.S. Pat. No. 7,867,981 issued on Jan. 11, 2011, which claims priority to International Application No. PCT/US2003/031390, filed on 3 Oct. 2003, which in turn claims priority to U.S. Patent Application No. 60/415,671, filed on 3 Oct. 2002. The contents of all the above applications are incorporated herein by reference.

FIELD OF THE INVENTION

The present invention generally relates to the field of highly purified amphotericin B (amphotericin BHP) compositions, and methods of use thereof.

More specifically, the present invention relates to the treatment of fungal infections in mammals using amphotericin B compositions of the present invention.

The present invention also relates to methods of making amphotericin B compositions. The purification techniques of the present invention allow for the isolation of polyene antifungals from the supernatant of *Streptomyces nodosus* cultures.

BACKGROUND OF THE INVENTION

Amphotericin B products are used to treat a variety of fungal infections, including systemic fungal infections.

Currently, polyenes are a major drug of choice for serious, disseminated fungal infections. Yet, the usefulness of polyenes is often limited by a lack of efficacy and by significant toxicity. These considerations, together with the predicted increased incidence of disseminated fungal infections, provide a strong impetus for the development of new antifungal therapies or improvement of existing ones. In regard to the latter approach, multiple polyenes are produced by *Streptomyces noduses* and could be useful as lead compounds. The present inventors observed antimycotic activity by many of these polyene compounds, but their cellular toxicity appeared high relative to the polyene compound known as amphotericin B (AmB). AmB is commercially available in a variety of formulations, however the active pharmaceutical ingredient called AmB contains other polyene compounds in addition to the compound known as AmB. The present inventors discovered that some of these non-AmB polyenes and perhaps other contaminants present in commercial AmB formulations were responsible for enhanced adverse effects of the drug (J. D. Cleary, R. Kramer, E. Swiatlo, and S. W. Chapman, Abstr. 45th Intersci. Conf. Antimicrob. Agents Chemother., abstr. F498, 2005).

Although the present invention encompasses many pharmaceutical formulations, AmB is used primarily in intravenous formulations in the treatment of severe fungal infections. However, its usefulness is compromised by a high incidence of adverse effects [flu-like symptoms (fever, chills, myalgias), capillary leak syndrome (hypotension, decreased organ perfusion), pulmonary congestion, changes in mental status (lethargy, confusion, agitation), renal dysfunction with secondary hypokalemia, hypomagnesemia and anemia, and liver dysfunction]. These adverse reactions are observed in up to seventy percent of treated patients. The mechanisms responsible for these reactions are, to date, not entirely known.

Yet, today (and for the past 40 years) AmB remains the best or only alternative for critically ill patients. Excerpts from the AmB boxed warning include the following:

Contraindications

This product is contraindicated in those patients who have shown hypersensitivity to amphotericin B or any other component in the formulation unless, in the opinion of the physician, the condition requiring treatment is life-threatening and amenable only to amphotericin B therapy.

Warnings

Amphotericin B is frequently the only effective treatment available for potentially life-threatening fungal disease. In each case, its possible life-saving benefit must be balanced against its untoward and dangerous side effects.

Precautions

Amphotericin B should be administered intravenously under close clinical observation by medically trained personnel. It should be reserved for treatment of patients with progressive, potentially life-threatening fungal infections due to susceptible organisms (see INDICATIONS AND USAGE).

Acute reactions including fever, shaking chills, hypotension, anorexia, nausea, vomiting, headache, and tachypnea are common 1 to 3 hours after starting an intravenous infusion. These reactions are usually more severe with the first few doses of amphotericin B and usually diminish with subsequent doses.

Rapid intravenous infusion has been associated with hypotension, hypokalemia, arrhythmias, and shock and should, therefore, be avoided (see DOSAGE AND ADMINISTRATION).

Amphotericin B should be used with care in patients with reduced renal function; frequent monitoring of renal function is recommended (see PRECAUTIONS, Laboratory Tests and ADVERSE REACTIONS). In some patients hydration and sodium repletion prior to amphotericin B administration may reduce the risk of developing nephrotoxicity. Supplemental alkali medication may decrease renal tubular acidosis complications.

Since acute pulmonary reactions have been reported in patients given amphotericin B during or shortly after leukocyte transfusions, it is advisable to temporally separate these infusions as far as possible and to monitor pulmonary function (see PRECAUTIONS, Drug Interactions).

Leukoencephalopathy has been reported following use of amphotericin B. Literature reports have suggested that total body irradiation may be a predisposition.

Whenever medication is interrupted for a period longer than seven days, therapy should be resumed by starting with the lowest dosage level, e.g., 0.25 mg/kg of body weight, and increased gradually as outlined under DOSAGE AND ADMINISTRATION.

As can be seen from the label information, AmB is used to treat a variety of life threatening infections despite very serious and dangerous side effects.

The United States Pharmacopeia (USP) has established quality standards for AmB used in pharmaceutical formulations. The USP allows AmB used as an active ingredient in pharmaceutical formulations to contain up to 25% impurities, including multiple polyene components. Unlike most active pharmaceutical ingredients, which have impurity levels less than 1%, AmB is not a single compound with very low impurity levels. See, for example, *J. Antimicro Chemother* 2007

60(6): 1331-1340. To comply with the USP, AmB formulations must have a potency of not less than 750 micrograms in 1 mg of material, a purity of 75%. Despite the fact that AmB, USP may contain only 75% of the polyene compound known as AmB, the entire pharmaceutical formulation is labeled "amphotericin B" as though it were all the active ingredient.

By discovering the source of the side effects, the present inventors have met a long-felt need in allowing a safer product. This was previously not known, and is surprising when compared to the many prior attempts to formulate a safer AmB product by adding other components to AmB containing formulations in hopes of reducing toxic effects or by using other drug products concurrently to reduce some of the side effects. Researchers in the field did not understand the underlying cause of the side effects despite over 40 years of dealing with significant adverse effects caused by the therapeutic use of AmB formulations. Thus, even though there were prior attempts to "purify" AmB formulations, there was no motivation to use the methods of the present invention, and there was no motivation to remove non-amphotericin B polyenes from the formulation. As stated above, it was the present inventors that discovered that the non-amphotericin B polyenes should be removed from AmB.

Through molecular biologic techniques, the present inventors have identified inflammatory cytokine genes that are up-regulated (increased in cells) after exposure to AmB. The genes include interleukin-1, a potent inflammatory cytokine. The adverse effects associated with stimulation of interleukin-1 are discussed below.

Proposed mechanisms of AmB-induced "flu like syndrome" include the expression of interleukin-1 (IL-1), tumor necrosis factor (TNF) or prostaglandins by mononuclear cells which then alter the hypothalamic set point inducing fever and chills. Administration of endotoxin causes similar reactions AmB exposure to mononuclear cells induces unique morphological changes and dramatically altered protein expression. Some host cell proteins have been reported to be inducible by AmB, such as TNF-α and IL-1β. The present inventors have demonstrated that this protein expression is not associated with release of preformed protein; protein release is associated with up-regulation of a gene or derepression of an inhibitory gene.

Currently, pharmacologic agents used to prevent AmB adverse reactions only address small aspects of the problem. Hydrocortisone is used to prevent the flu-like syndrome and hypotension. Acetaminophen is also used to prevent the flu-like syndrome. Fluids administered parenterally are used to prevent renal dysfunction. Also, lipid products have been developed to decrease the toxicity of AmB. These products encapsulate AmB in an attempt to reduce side effects. However, they are not totally successful.

What is needed, then, is an AmB active pharmaceutical ingredient that can be used in a variety of formulations without the high incidence of side effects.

SUMMARY OF THE INVENTION

One aspect of the present invention is the discovery of an improved method of isolation of the AmB compound with reduced amounts of non-AmB components. As shown herein, AmB compositions of the present invention are associated with decreased toxicity in mammals and cells. Thus, the present invention allows for reduced adverse reactions when using AmB formulations.

In certain embodiments of the present invention, highly purified amphotericin B (AmBHP) is obtained from high pressure liquid chromatography fractionation.

Disclosed herein are pharmaceutical compositions comprising the AmB compound while being substantially free of non-AmB polyenes.

Another embodiment of the present invention is a method of treating fungal infections in a mammal, comprising administering a therapeutically effective amount of a composition of the present invention, being substantially free from non-AmB polyenes, and a pharmaceutically acceptable carrier to a mammal in need thereof.

Another embodiment of the present invention is a method of testing toxicity in patients treated with pharmacological agents. This embodiment includes a method of testing patients treated with AmB.

Another embodiment of the present invention is a pharmaceutical composition comprising an AmB formulation, wherein the composition comprises 90% or more of the compound, AmB and 10% or less non-AmB polyenes.

One embodiment of the present invention demonstrates semi-preparative high pressure liquid chromatography (HPLC) procedures for the isolation of AmB and other polyene components from commercially available AmB formulations. For example, as shown below, Pharma-Tek® is a commercial deoxycholate-based AmB formulation. Pharma-Tek® is readily available, affordable, and representative of other deoxycholate-based formulations in its profile and the relative amounts of non-AmB polyene "contaminants". This commercial formulation and embodiments of the present invention were assessed in vitro and in vivo.

One embodiment of the present invention is a method of ameliorating AmB treatment side effects that comprises providing a formulation that comprises a polyene active ingredient that includes the AmB compound, with the structure shown below:

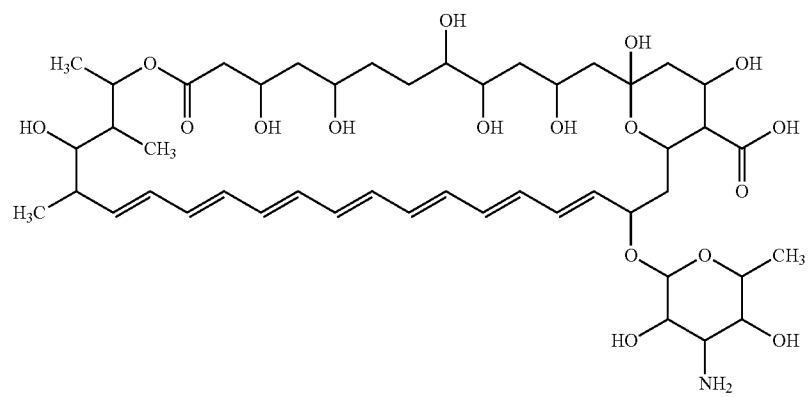

wherein the AmB compound is present, in terms of polyene content, in an amount greater than 90%, and non-AmB polyene compounds in an amount of no greater than 10%, and a pharmaceutically effective carrier; and administering a therapeutically effective amount of said formulation to a subject in need thereof.

Another embodiment of the present invention is a method of making an AmB formulation, comprising:

providing USP compliant AmB;

introducing the AmB into a liquid chromatography column;

isolating a polyene solute that comprises, in terms of polyene content,

AmB compound in an amount greater than 90%, and non-AmB polyene compounds are present in an amount of no greater than 10%, and collecting the solute and combining the solute with a pharmaceutically acceptable carrier.

These and other embodiments will be apparent to one of ordinary skill in the art when reading the specification and claims.

DETAILED DESCRIPTION OF THE INVENTION

Figure 1:
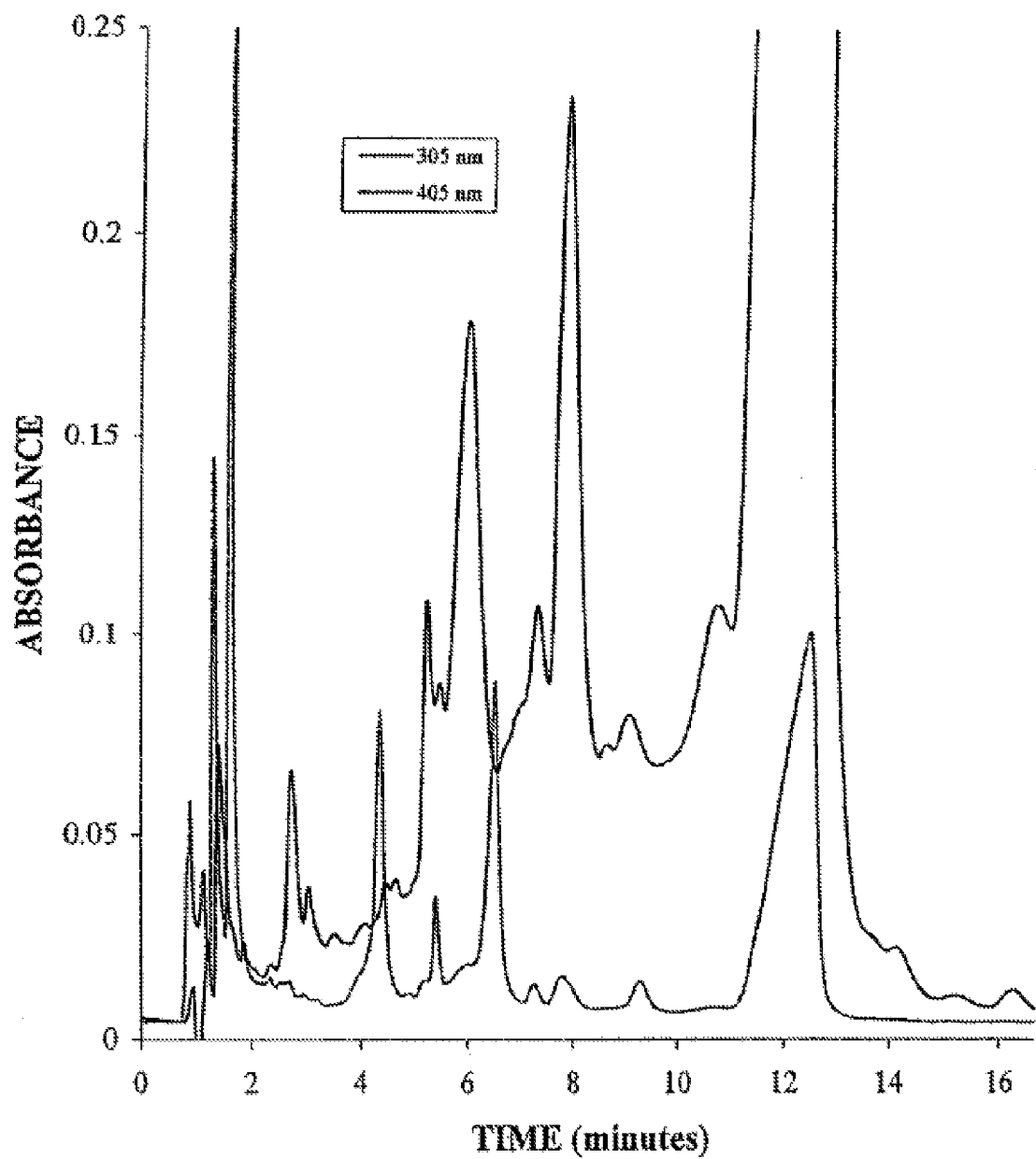
FIG. 1 is a graph that shows HPLC fractions.

As indicated above, while prior art, AmB, has been recognized as a valuable material, particularly in its powerful antifungal properties, its clinical (i.e. therapeutic) use has been limited because of the severe side effects to the subject being treated.

AmB is insoluble in aqueous solution. Consequently it is supplied commercially as a combination of AmB, lipid carriers, desoxycholate and/or buffers, suspended in a glucose solution to form a colloidal suspension for administration to the patient. It is usually given intravenously over a period of from two to six hours. Faster infusions may result in cardiotoxicity. Other toxic effects of AmB may manifest themselves as renal dysfunction, anemia, fever and hypotension.

Thus, embodiments of the present invention, which have a high AmB compound content and low impurity content, greatly reduce the toxicity of standard AmB treatment. The compositions of the present invention are substantially free from non-AmB polyene contaminants and endotoxins—sources of the side effects mentioned herein.

The toxicity of AmB limits the total amount of the drug which may be used in the treatment of a fungal infection. Furthermore, it is often ineffective in neutropenic and immunodeficient patients, patients who are highly susceptible to fungal infections. Consequently, there is a need for a system which decreases the toxicity of AmB to the mammalian system while simultaneously enhancing its effectiveness against the fungal infection.

Definitions

As used in the specification and the appended claims, the singular forms "a," "an" and "the" include plural referents unless the context clearly dictates otherwise. Thus, for example, reference to "a polyene" includes mixtures of two or more such polyenes.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, the term "Amphotericin B" or "AmB" refers to an active pharmaceutical ingredient that comprises the AmB compound as well as significant and harmful amounts of non-AmB polyenes. As discussed herein, "formulations" commonly referred to as an "AmB formulation" or "AmB composition" comprise other non-AmB polyenes and pharmaceutically acceptable carriers.

As used herein, the term "AmB compound" refers to the following compound, and isomers thereof:

the other side of the ring. Their structures also often have a d-mycosamine (a type of amino-glycoside) group bonded to the molecule. The series of conjugated double bonds typically absorbs strongly in the ultraviolet-visible region of the electromagnetic spectrum, often resulting in the polyene antibiotics having a yellow color.

As used herein, the term "Amphotericin B Highly Purified" and "AmBHP" as used herein refers to AmB that comprises, in terms of polyenes, at least 90% AmB compound, and no more than 10% non-AmB polyenes. Embodiments of the present invention include compositions that, in terms of polyenes, 90, 91, 92, 93, 94, 95, 96, 97, 98, 99, or 100% of the AmB compound, with the remainder being non-AmB polyenes and other impurities.

The term "endotoxins" refers to byproducts or parts of bacterial degradation or growth.

As used herein, the term "impurity," in connection with AmB and AmB formulations, refers to endotoxins and/or non-AmB polyenes and other compounds present in an AmB.

The term "USP grade AmB" refers to AmB compositions that comply with the National Formulary of the United States Pharmaceopeia (USP 31 NF 26, Volume 2 (2008)).

As used herein, the term "substantially pure AmB" refers to compositions containing greater than about 90% of the AmB compound. Preferably, substantially pure compositions contain greater than about 96% AmB compound. In other embodiments, the compositions of the present invention contain greater than about 97, 98, or 99% AmB compound.

As used herein, "AmB Formulation" is a pharmaceutical composition for administration to a subject that contains AmB.

As used herein, "AmBHP Formulation" is a pharmaceutical composition for administration to a subject that contains

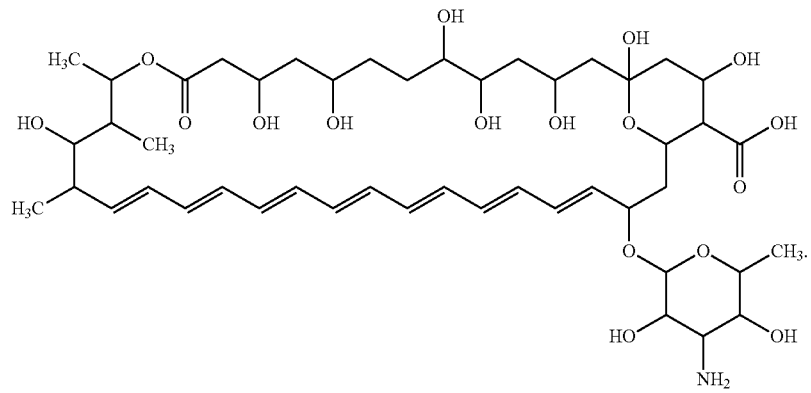 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

As used herein, the term "polyene" refers to poly-unsaturated organic compounds that contain one or more sequences of alternating double and single carbon-carbon bonds. Polyene antimycotics, sometimes referred to as polyene antibiotics, are a class of antimicrobial polyene compounds that target fungi. These polyene antimycotics are typically obtained from some species of *Streptomyces* bacteria. The polyenes bind to ergosterol in the fungal cell membrane and promote leakiness which may contribute to fungal cell death. AmB, nystatin, and natamycin are examples of polyene antimycotics. Their chemical structures feature a large ring of atoms (essentially a cyclic ester ring) containing multiple conjugated carbon-carbon double bonds (hence polyene) on one side of the ring and multiple hydroxyl groups bonded to AmBHP. Embodiments include compositions that comprise AmBHP as an active ingredient and a pharmaceutically acceptable carrier.

It has recently been shown that the encapsulation of certain drugs in lipid carriers before administration to the patient can markedly alter the pharmacokinetics, tissue distribution, metabolism and therapeutic efficacy of these compounds. Further, the distribution and pharmacokinetics of these drugs can be modified by altering the lipid composition, size, charge and membrane fluidity of the lipid carriers in which they are encapsulated.

The substantially pure compositions of the present invention may be used as active pharmaceutical ingredients in AmB pharmaceutical formulations, and may be administered in accordance with known procedures of administering AmB formulations to a subject.

For example, the AmBHP of the present invention may be formed into a lipid formation as an improvement to commercially available USP grade AmB containing lipid formulations. Commercially available AmB lipid formulations complex AmB with a lipid component that enables solubility in aqueous solutions, thus allowing for parenteral administration. Over the past two decades, researchers have investigated the utility of incorporating AmB into phospholipid vesicles (liposomes) and/or cholesterol esters in order to provide larger amounts of parent drug and concomitantly, less nephrotoxicity. To date, at least three lipid formulations of AmB are commercially available. AmB lipid complex (ABLC, Abelcet); AmB cholesteryl sulfate complex, also called AmB colloidal dispersion (ABCD, Amphotec); and liposomal AmB (L-AmB, AmBisome). The present invention may be used instead of AmB in these commercially available formulations, and one of ordinary skill in the art would understand how to substitute the AmBHP of the present invention for AmB in the commercially available lipid formulations.

The current United States Food and Drug Administration (FDA) approved dosages for the three lipid formulations are believed to be as follows: L-AmB, 3-5 mg/kg/day; ABLC, 5 mg/kg/day; and ABCD, 3-4 mg/kg/day. The lipid formulations can safely be administered at daily dosages 5 to 10 fold higher than the daily dosages of AmB.

The following chart identifies commercially available AmB formulations in which the AmBHP of the present invention can be substituted for AmB currently in use:

TABLE 1

Examples of Commercially Available AmB Formulations

| Generic Name | Trade Name | Manufacturer/Marketer | FDA |
|---|---|---|---|
| Amphotericin B deoxycholate (AmBD) | Amphotericin B | (generic) | 1958 |
| Amphotericin B lipid complex (ABLC) | ABELCET ™ | The Liposome Company | 1995 |
| Amphotericin B cholesteryl sulfate complex, amphotericin B colliodal dispersion (ABCD) | AMPHOTEC ™ | SEQUIS Pharmaceuticals | 1996 |
| Liposomal amphotericin B (L-AmB) | AMBISOME ™ | Fujisawa USA and NeXstar Pharmaceuticals | 1997 |

The chemical properties and physical characteristics of available AmB products are outlined in the Table 2, below:

The AmBHP containing formulations of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

In other embodiments, AmBHP containing formulations of the present invention may be administered to a patient in an amount ranging from about 0.01 milligrams per kilogram of body weight per day to about 100 mg per kg per day, including all intermediate dosages there between.

In yet other embodiments of the present invention, the AmBHP containing formulations of the present invention may be administered to a patient in an amount ranging from about 0.1 milligrams per kilogram of body weight per day to about 10 mg per kg per day, including all intermediate dosages there between.

The AmBHP containing formulations of the present invention may be administered by any known route, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such formulations may be administered as pharmaceutically acceptable formulations that include pharmaceutically acceptable carriers, buffers or other excipients. The phrase "pharmaceutically acceptable" refers to molecular entities and compositions that do not produce an adverse, allergic or other untoward reaction when administered to a human. For treatment of conditions of the lungs, the preferred route is aerosol delivery to the lung via bronchoalveolar lavage or the like.

Of course, with respect to conventional AmB therapy, intravenous injection and/or infusion appears to be the most popular delivery route. In such embodiments, the AmBHP may be administered gradually over a period of time ranging from 0.001 h to 100 h. In other embodiments, when administration of the pharmaceutical formulations of the present invention via intravenous injection and/or infusion is the preferred route, the pharmaceutical formulations of the present invention should be administered gradually over a period of time ranging from 0.1 h to 50 h. In other embodiments, when administration of the pharmaceutical formulations of the

TABLE 2

Chemical and Physical Properties of Examples of AmB Formulations

| | Lipid Configuration | Size (Nanometers) | Lipid Component | AmB content (mol %) |
|---|---|---|---|---|
| AmBD | Micelle | <25 | sodium deoxycholate | — |
| ABLC | Ribbon-Like | 500-5000 | dimyristoylphosphatidylcholine dimyristoylphosphatidylglycerol | about 33% |
| ABCD | Disc-Like | 125 | cholesteryl sulfate | about 50% |
| L-AmB | Unilamellar vesicle (spherical) | 90 | hydrogenated phosphatidylcholine cholesterol distearoylphospohatidlglycerol | about 10% | present invention via intravenous injection and/or infusion is the preferred route, the pharmaceutical formulations of the present invention should be administered gradually over a period of time ranging from 1 h to 10 h.

As stated above, the AmBHP of the present invention may be part of an HDLC (high drug:lipid ratio complex). As one example of this embodiment, the AmBHP of the present invention may be used in the same manner as the AmB complex disclosed in U.S. Pat. No. 6,406,713, incorporated herein by reference. Those embodiments include HDLC systems which comprise lipids and bioactive agents including drugs. Such HDLCs may comprise phospholipids such as DMPC and DMPG, preferably in a 7:3 mole ratio or saturated phospholipids or fatty acid phospholipids. The bioactive agent for these embodiments is the highly purified AmB (AmBHP) of the present invention. Examples of the mole percent of the AmBHP includes examples where the amount is from about 6 to about 70 mole percent. Other examples are in the about 30 to about 50 mole percent range. Pharmaceutical formulations of the HDLCs of the present invention may be made comprising pharmaceutical acceptable carriers, and these formulations may be administered parenterally. Of course, such formulations are used to treat infectious diseases such as fungal infections, by administering them to mammals such as humans. The HDLC-containing formulations using AmBHP of the present invention include those compositions substantially free of liposomes and compositions substantially free of liposomes entrapping the drug. The term "substantially free" in this context shall be taken to mean generally no more than about 10 percent by weight of liposomes, no more than about 5%, and/or no more than about 3%.

Various methods for preparing HDLC formulations containing AmB are disclosed in the US '713 patent, including, for example, techniques that first solubilize the AmB in a solvent such as DMSO or methanol.

In an alternative method, lipid particles (or liposomes) containing AmB containing about 6 percent to 50 mole percent AmB are formed and then the particles (or liposomes) are subjected to a heating cycle, at about 25° C. to about 60° C. Such a cycle forms a more highly ordered and less toxic AmB/lipid complex.

As further examples, the AmBHP of the present invention may be used in the manner and amounts described in U.S. Pat. Nos. 3,965,090; 4,663,167; 4,766,046; 4,054,734; 5,965,156; 4,049,898; 5,194,266; and 4,035,568, all of which are incorporated herein by reference.

One of ordinary skill in the art would readily understand that formulations taught in the art that contain AmB are suitable for use for AmBHP requiring only routine optimization studies.

The mode of administration of a preparation of the present invention may determine the sites and cells in the organism to which an AmBHP composition will be delivered. Generally speaking, AmBHP of the present invention will be administered in a mixture with a pharmaceutically acceptable carrier selected with regard to the intended route of administration and standard pharmaceutical practice. For instance, delivery to a specific site may be most easily accomplished by topical application (if the infection is external, e.g., on areas such as eyes, skin, in ears, or on afflictions such as wounds or burns). Such topical applications may be in the form of creams, ointments, gels, emulsions, or pastes, for direct application to the afflicted area. Alternatively, the preparations may be injected parenterally, for example, intravenously, intramuscularly, or subcutaneously. For parenteral administration, they can be used, for example, in the form of a sterile aqueous solution which may contain other solutes, for example, enough salts or glucose to make the solution isotonic. Other uses, depending on the particular properties of the preparation, may be envisioned by those skilled in the art.

For therapeutic administration to humans, the prescribing physician will ultimately determine the appropriate dosage for a given human subject, and this can be expected to vary according to the age, weight, and response of the individual as well as the nature and severity of the patient's symptoms. In the curative or prophylactic treatment of fungal or viral diseases, the dosage of AmBHP in the HDLC or liposomal form will generally be about that employed for the free drug. In some cases, however, it may be necessary to administer dosages outside these limits. The prescribed amount may vary when used for curative and prophylactic treatment of fungal or other infectious diseases.

It is generally accepted that the initial action of AmB occurs at the level of the plasma membrane and results in the formation of pores of sufficient diameter to allow transmembrane movement of monovalent ions. This mechanism of action is independent of cell type, contributing to both the efficacy of AmB against fungi and its toxicity toward mammalian cells. Consequently, conclusions about AmBHP formulations of the present invention inferred from the results should be applicable not only to experimental cell (e.g., monocytes) but also to other human cell types (e.g., renal tubular cells). A series of ensuring events can be predicted which contribute to the toxicity and immunomodulatory actions of AmB. Those events are (a) an influx of $Na^+$ and depolarization of the plasma membrane, (b) activation of voltage-dependent $Ca^{2+}$ channels, (c) increased [Ca]c, and (d) a calcium-dependent increase in expression and secretion of specific cytokines (e.g., IL-1β). Although an efflux of potassium has been associated with its antifungal effects (1), AmB has been reported to cause membrane depolarization (14,20). The latter event is consistent with a net influx of sodium. Influx of sodium and the resulting depolarization of the plasma membrane can also account, through activation of voltage-dependent calcium channels, for the increase in [Ca]c noted in human monocytic and glomerular mesengial cells caused by AmB (22,23). Increased [Ca]c can, in turn, contribute to the oxidative stress attributed to AmB as well as its overall cytotoxicity.

The premise that the ionophoretic effects of AmB leads to activation of voltage-dependent calcium channels, secondary to $Na^+$ influx and membrane depolarization, would predict a self-limiting, regulated response (calcium signal) because of channel inactivation and other compensatory mechanisms. Bulk movement of calcium into the cell because of a general loss of membrane integrity, on the other hand, should be reflected by a progressive increase in [Ca]c and lead to a cytotoxic response. Data presented in this communication and previously (22) indicate that the former is true for the calcium signal elicited by generic (Pharma-Tek®) AmB. Likewise, a limited, but sustained, increase in [Ca]c in TPH-1 cells was caused by AmB compositions of the present invention (see FIG. 10, discussed in Example 2). However, the calcium signal caused by AmBHP of the present invention is indistinguishable from that caused by Pharma-Tek® AmB. One could have predicted that removal of some of the ancillary components present in AmB would reduce or at least alter the calcium signal. The fact that it did not argues that an increase in [Ca]c is a general response to all polyenes. It is likely that a rise in [Ca]c is an obligatory consequence of the mechanism of AmB action and that a calcium signal per se is not a good predictor of cytotoxicity.

The cytotoxic effects of AmBHP of the present invention were also evaluated by measurement of [$^3$H]thymidine incorporation by THP-1 cells. Both Pharma-Tek® AmB and AmBHP caused concentration-dependent reductions in thymidine incorporation. In general, the reductions in thymidine incorporation caused by AmBHP were not distinguishable from those caused by Pharma-Tek® AmB. At face value, these data do not support the contention that AmBHP is less toxic. But, neither was it more toxic, even at concentrations as high as 20 µM. In fact, within the therapeutic range, inhibition of thymidine uptake occurred at a 2-fold lower concentration of AmB than of AmBHP. Given the general mechanism of action of AmB, the cytotoxic and non-cytotoxic effects of the drug most likely can not be fully resolved. Even so, data from in vitro measurements of toxicity contrast significantly with data on the relative toxicity of AmBHP assessed in vivo. The positive effects of AmBHP on survival and renal function relative to other AmB formations, coupled with equal or better efficacy, seem more relevant to its potential as a safer therapeutic agent for treatment of disseminated fungal infections. The explanation for the apparent difference in the toxicity of AmBHP in vitro and in vivo is not readily apparent. It is possible that differences in cytotoxicity between AmBHP and preparations containing significant amounts of non-AmB polyenes such as Pharma-Tek® AmB would be apparent in a different cell type, e.g., a renal epithelial cell. Also, the kinetics of AmBHP and non-AmB polyene components present in commercially available AmB formulations might be different. Be that as it may, perhaps the most telling indication for the potential of AmBHP as a safer active pharmaceutical ingredient for use as an antifungal agent in vivo is the relatively modest increase IL-1β production by monocytic cells in response to it when compared to the much greater response caused by commercially available AmB.

Drug-associated renal dysfunction is among the most clinically important AmB side effects. Researchers have estimated that up to 80% of patients receiving AmB will experience an episode of renal impairment during prolonged treatment. A recent multivariate analysis of risks for AmB-related nephrotoxicity identified cumulative dose of AmB and concomitant receipt of other nephrotoxic drugs (particularly, cyclosporine) as major predictive factors. In bone marrow transplant patients, use of hemodialysis was associated with a greater risk of death (OR 3.1), as were the duration of AmB treatment (OR 1.03 per day) and the use of other nephrotoxic agents (OR 2.0). In the studies reported herein, glomerular filtration rate (GFR) and other indices of renal function in response to infusion of AmBHP were comparable to those caused by a 10-fold lower dose of AmB. Importantly, baseline values for GFR in our studies were within the standards reported by other using the same model (18). In addition, changes in renal function associated with AmB were consistent with other known pharmacologic and physiologic events. In our model, AmBHP, at 10-fold higher doses, induced similar changes in renal function compared to AmB.

Finally, assessment of efficacy was completed in a routine, murine, disseminated candidiasis model, and the data obtained allow for some important comparisons between AmBHP and commercially available AmB. First, AmBHP causes less overall toxicity in vivo, as evidence by a decrease in mortality, than does AmB. The $LD_{50}$ in mice for AmB has been evaluated and published for multiple breeds. The average parenteral dose identified as the $LD_{50}$ was 2.78 mg/kg (range 2.3-3.46), with no apparent difference between OF-1, Albino Webster derived CD-1, and Balb/c mice. In the studies described here, all but one animal died within 24 h in response to this dose of generic AmB (n=10). There was a difference in fed or fasting animals; the $LD_{50}$ in fasting mice (1.51 mg/kg) was lower than the $LD_{50}$ in fed animals (2.38 mg/kg). Formulation of AmB into an emulsion ($LD_{50}$ 7.34 mg/kg), a lipid complex ($LD_{50}$>75 mg/kg) or a liposome ($LD_{50}$ 32.9 mg/kg) significantly improves the $LD_{50}$ when compared to AmB formulated with deoxycholate. Data obtained from 5 sets of mice indicate that the $LD_{50}$ for AmBHP (~5 mg/kg) is at least twice that of AmB (~2.5 mg/kg) (data not shown). Second, our data indicate that when doses are titrated within a non-lethal range, AmBHP formulations are as effective as AmB formulations in controlling *Candida* infection. Moreover, reduction in tissue burden achieved with AmBHP is associated with improved survival.

Pharmacoeconomic assessments of the cost of using AmB have yielded frightening results. An estimated 30% of patients treated for systemic fungal infections will experience severe renal dysfunction (renal failure) and will require, on average, an additional 8.2 days of hospitalization along with a secondary 2- to 2.7-fold increased risk of death. The cost of AmB-induced events was $29,823 per case. The use of lipid-based formulations of AmB, secondary to their lower risk for nephrotoxicity, is replacing conventional AmB therapy for treatment of systemic fungal infection except in many HIV-infected and pediatric patients. Yet, the cost of comparable therapy is considerably greater for the lipid formulation; daily cost for AmB averages $25, whereas that for lipid-formulated AmB ranges between $450 and $1850. Assuming a 14-day course of therapy, a patient will pay an average of $7000 more for a lipid-based, albeit safer, AmB product.

Accordingly, it is clear that the present invention satisfies a long-felt need.

EXAMPLES

The following examples are submitted to show embodiments of the present invention. They are intended to show embodiments of the present invention and be exemplary of aspects of the present invention and not intended to be limiting thereof.

The examples illustrate other embodiments of the present invention and are designed as an in vitro evaluation of AmB components fractionable through high pressure liquid chromatography using the described methods.

Example 1

This Example shows the preparation of embodiments of the present invention. In this example, commercially available AmB, with the typical presence of at least one non-AmB polyene, is purified to provide a composition that, in terms of polyene content, is at least 90% AmB compound and no more than 10% non-AmB polyene and other impurities.

Aliquots of about 11.2 mg of powder are measured from commercial grade AmB manufacturers. In this example, AmB manufactured by Apothecon and Sigma are utilized. These aliquots contain about 5 mg of AmB. Each sample is stored at about 4° C. in microcentrifuge tubes and diluted immediately prior to each experiment. The 5 ug/mL dilution is made by adding about 1.0 mL sterile water to each aliquot. The 2.5 ug/mL is made by using about a 2:1 dilution of about 500 uL of the 5 ug/mL stock. The Sigma brand is not a pharmaceutical grade product and is selected as a positive control representing a "minimally purified" product. Fresh aliquots are diluted prior to each experiment and agitated immediately before use. A sample aliquot from each AmB preparation is reserved for testing endotoxin contamination.

Other pharmacologic agents utilized include *Escherichia coli* endotoxin (Serotype 026:b6 lipopolysaccharide, Sigma; St. Louis, Mo.) (LPS), desoxycholate and sodium phosphate buffer which are obtained from Sigma. These reagents are used as positive and negative controls for IL-1β expression from mononuclear cells. Reagents used in the IL-11β expression assay are diluted with sterile water so that 0.01 ml of stock solutions added to culture wells resulted in the final concentrations noted.

Unsupplemented media (RPMI-1640) is obtained from Flow Laboratories (McLean, Va.). Mononuclear cells [THP-1; ATCC 222:U937] are resuspended to a final concentration of approximately $5 \times 10^6$ cells/mL in supplemented media (RPMI-1640, about 10% autologous serum, about 100 ug/mL streptomycin and about 100 u/mL penicillin). About one milliliter of mononuclear cells is seeded in Limbro 24-well plates (Flow Laboratories; McLean, Va.) and incubated for 24 hours at 37° C. in 5% $CO_2$.

High Pressure Liquid Chromatography Isolation and Validation: AmB aliquots of Example 1 are applied to a 4.6×150 mm 5 micron AquaC18™ column (Phenomenex®), and components resolved isocratically using about 70% methanol:about 30% 5 mM sodium citrate (pH 7.0) (vol:vol) flowing at a rate of about 1 ml per minute. Column eluant is monitored at about 305 nm and about 405 nm. Specific composition of the solvent varies from about 70:30 (methanol:sodium citrate) to about 75:25 (methanol:sodium citrate) to achieve the best resolution of the AmB compound and other components yielding AmBHP.

Viability Assay: AmB fractions are tested for effects on human cell viability. A tritiated thymidine incorporation assay in addition to Erythrocin red or Trypan Blue exclusion dye tests is used. Assays of cytotoxic activity using tritiated thymidine are performed under aerobic conditions. Substances to be assayed are diluted in RPMI containing about 10% human or bovine serum, added to the first vertical column of a 96-well flat-bottom tissue culture plate, and serially diluted in RPMI in the remaining wells of each row using a multi-tip pipetter. Control rows without drugs or containing solubilizing agents (DMSO, DOC, glycerin) are similarly treated so that the concentrations of these diluents are similarly decreased across the plate. Logarithmic growth phase THP-1 cells are added (about $10^6$ cell per well), and the plates maintained in a $CO_2$ incubator (about 5% $CO_2$ in air; about 37° C.) for about 24 hours. At the end of this drug-exposure phase, the plates are centrifuged about 5 min at about 200×g, the supernatants are briskly decanted, and the wells refilled with PBS. After the third such rinse, the wells are refilled with drug-free RPMI. The plates are returned to the $CO_2$ incubator, and any remaining viable cells allowed to grow during a 24-hour amplification phase. The plates are then centrifugally washed twice with PBS, and the wells refilled with RPMI-1640 (Sigma) containing about 10% FBS and about 5 mCi/well [methyl-$^3$H] thymidine (New England Nuclear, Boston, Mass.) and incubated for about an additional hour. The plates are then harvested to glass-fiber paper using distilled water rinses, and the paper counted with a Matrix$_{96}$ gas-ionization direct-beta counter (Packard Instrument Co, Meriden Conn.). Each drug exposure is done in triplicate rows of a single plate. Each plate included controls for the cytotoxicity of solubilizing agents (DMSO, DOC, glycerin) and a drug-free control. Radioactivity per well is analyzed with Microsoft-Excel. The assay differentiates target cell death from drug-induced loss of motility since it measured incorporation of radioactivity into newly synthesized DNA after drug washout. Minimum lethal concentration (MLC) is defined as the lowest concentration of drug (in a 1:2 serial dilution series) to kill all the target cells (reduce incorporation to background levels). The 100% control level (no killing) for each plate is defined as the mean radioactivity per well of the drug-free control row.

Experimental results are expressed as percent of the control mean using the drug-free control as 100%. This assay is adapted for use with mammalian cells in tissue culture monolayers by substituting DME containing 10% FBS for the RPMI and by extending the tritiated thymidine pulse labeling period in RPMI/10% FBS to an overnight incubation.

In vitro Infusion Related Reaction Assay AmB is added to Limbro 24-well plates at final concentrations of about 0 ug/mL and 20 ug/mL. Cells are then incubated for about 2 hours. Supernatants are collected from each well after three freeze-thaws and stored at about −70° C. until assay. Samples are assayed for IL-1β using an enzyme-linked immunosorbent assay (Cistron Biotechnology; Pine Brook, N.J.) (ELISA). The procedure involves a four-step test carried out in microtiter wells which are coated with IL-1β specific monoclonal antibody. Manufacturer's data indicate an assay sensitivity of 20.0 pg/mL and a specificity for IL-1β. There is no cross-reactivity for IL-1α, IL-2, TNF-α or interferon. Evaluations of assay precision demonstrate a coefficient of variation of about 5.3% to about 6.7% for intra-assay variability and about 6.6% to about 8.4% inter-assay variability. Data are the mean of duplicate assays and are expressed in pg/mL on the basis of standards supplied by the manufacturer.

AmB Compound Assay: A polyclonal rabbit antibody is isolated from New Zealand white rabbits after standard immunization with AmB complexed with an immune adjuvant, Keyhole Limpet Hemocyanin. An anti-AmB antibody is purified by filtering serum through an Aminolink Affinity-Pak Column (ImmunoPure Ag/Ab; Pierce Chemical Co., Rockford, Ill.), diluted to a final concentration of 180 ug/mL and frozen at about −70° C. until further use. The ELISA is initiated by removing a light protection cover from an AmB-bovine serum albumin coated microtiter plate. The 1.0 ug/mL coating solution is emptied, and triplicate well washings are performed. Wash solution consisted of a standard phosphate buffered salt solution containing tween. The 96-well plates are then blocked with bovine serum albumin for one hour at about 37° C. and again thrice washed. Addition of amphotericin solution (100 uL) is followed by Anti-AmB antibody (100 uL) and then incubation for about an hour at about 37° C. Plates are emptied and thrice washed. Horseradish peroxidase-anti-rabbit IgG diluted 1:1000 in buffer is added after blot drying. Plates are again incubated for an additional hour at about 37° C. and thrice washed. A 200 uL aliquot of peroxidase substrate solution [Fast-P-9187; Sigma Chemical, St. Louis, Mo.] is pipetted into each well, and ELISA plates are tested after about 10 minutes for photometric density [Dynatech multiscan; Flow Laboratories, McLean, Va.] utilizing a 405 nm filter. Finally, AmB-spiked samples are tested for stability during storage at about −70° C. for about 60 days. Triplicate light-protected samples at AmB concentrations of 2.5 ug/mL and 5 ug/mL are assayed by ELISA.

Published data indicate an assay sensitivity of 0.15 ug/mL. There is cross-reactivity for agents with polyene structures, nystatin and hamycin. Evaluations of assay precision demonstrates a coefficient of variation of 3.0% for intra-assay variability. Data are the mean of duplicate assays and are expressed in ug/mL on the basis of Apothecon brand as the standard.

Spectrophotometric Assay: Classification and quantification of a polyene can be performed based on each agent's ultraviolet absorption. The ultraviolet spectra for tetraenes (nystatin, amphotericin A compound) has characteristic peaks at about 290 nm, about 305 mu and about 318 mu, while heptaenes (amphotericin B compound) occurs at about 360 nm, about 378 nm and about 405 nm. The principles of Beer's Law are used to estimate the relative amount of amphotericin A or B compounds in each preparation. Nystatin is used in our assays for amphotericin A compound and tested at an optical density of about 290 nm. AmB formulated by Apothecon is tested at an optical density of about 360 nm. These optical densities are selected owing to their uniqueness to amphotericin A and B, respectively. Peaks at other optical densities are shared with pentaenes and hexaenes, making it difficult to preclude their existence in the solution. Two unique peaks for pentaenes are identified at optical densities of about 325 nm and about 333 nm. Samples of each amphotericin formulation are diluted in about 1.0 mL DMSO, then further diluted with about 5 mL methanol. A 400 uL aliquot from this dilution is further diluted in about 5 mL of methanol. A dilution of sodium deoxycholate does not affect the optical density measurements. Ultraviolet light absorbance from about 200 nm to about 450 nm is determined with a Gilford Spectrophotometer and analyzed by Response II software (Gilford; Dayton, Ohio). Data are the mean of triplicate assays, and amphotericin concentrations are expressed in micrograms per milliliter on the basis of Apothecon brand as the standard for AmB compound and nystatin as the standard for amphotericin A compound.

Antifungal Agents: Stock solutions of sample agents are prepared by dissolving stock powder in dimethyl sulfoxide (DSMO) and appropriately diluted using RPMI 1640 buffered to about pH 7.0 with about 0.165M morpholinepropanesulfonic acid (MOPS) (PML Microbiologicals, Wilsonville, Oreg.). The final concentration of DMSO is such that the concentration in test solutions comprised less than about 6% of the total solution composition.

Test Isolates: One *Candida albicans* isolate, American Type Culture Collection (ATCC) strain 90028, is selected.

DMSO inhibitory test: Effects of DMSO on MIC determination are tested using NCCLS broth microdilution guidelines and the test isolate *C. albicans* 90028. One hundred microliters of a DMSO and an RPMI solution are placed in the wells of a microdilution tray so that the concentrations of DMSO in tested wells are 1, 2, 3, 4, 5, 6, 7, 8, 9, 10, 15, 20, 25, and 30 percent. Yeast inoculum is prepared as described in antifungal susceptibility testing, and 100 ul are added to each test well. The trays are incubated in a humid, dark chamber for about 48 hours at about 35° C. The MIC is determined as any visible change in growth when compared to control. DMSO inhibitory tests are preformed in duplicate.

Antifungal Susceptibility Testing: Sample MIC's are determined by broth microdilution according to NCCLS guidelines. Isolates are subcultured twice on potato dextrose agar (PDA) plates (Remei, Lenexa, Kans., USA). Fungal suspensions are prepared by transferring four to five colonies into about 5 mL of sterile about 0.9% saline. The suspensions are standardized, using spectrophotometric methods, and diluted in RPMI 1640 buffered to about pH 7.0 with 0.165M MOPS (PML Microbiologicals, Wilsonville, Oreg.) to yield an initial inoculum of $0.5 \times 10^3$-$2.5 \times 10^3$ CFU/mL. 100 uL of inoculum is added to each well of a microtiter tray containing 100 uL of serially diluted drug in RPMI solution. Sample concentrations of about 0.0039, about 0.0078, about 0.0156, about 0.0312, about 0.0624, about 0.125, about 0.25, about 0.5, about 1, about 2, and about 4 ug/mL are achieved. The trays are incubated in a humid, dark chamber for about 48 hours at about 35° C. The MICs are recorded as the wells with 80% inhibition and 100% inhibition when compared to control. MIC determinations are performed a minimum of two times with an additional run if the quantity of sample drug allowed for it. It is decided to determine the MFC on samples which achieved definitive MICs. After the MIC is read at 48-h, a 1 uL sample is withdrawn from each microtiter tray with a 96 pin replicator (Boekel, Feasterville, Pa.) and plated onto an RPMI agar plate. Samples are incubated in a humid, dark chamber for about 48 hours at about 35° C. MFC is determined by the complete lack of organism growth on the plate and recorded as the corresponding well in the MIC tray.

An ANOVA is performed comparing Apothecon brand AmB formulation with Sigma brand AmB. A standard T-test is used to compare the differences identified within the ANOVA. An alpha of about 0.05 and a beta of about 0.2 are selected for this comparison. Sigma Stat [Jandel; San Dimas, Calif.] is utilized for the statistical analysis.

High pressure liquid chromatography of commercially available AmB leads to the identification of multiple polyenes and probably bacterial/fungal endotoxin (FIG. 1). Isolation of each peak at optical densities of about 305 nm and about 405 nm has led to the identification of these products as polyene compounds or endotoxin. The fractions are isolated from aliquots of commercially available AmB or Sigma brand AmB and resolve with using about 70% methanol:30% 5 mM sodium citrate (pH 7.0) (vol:vol) at a flow rate of about 1 mL/minute. The fraction elutes from the column at about 12 minutes from a 4.6×150 mm 5 micron AquaC18™ column monitored at about 305 nM and about 405 nM. This component is AmBHP.

Figure 2:
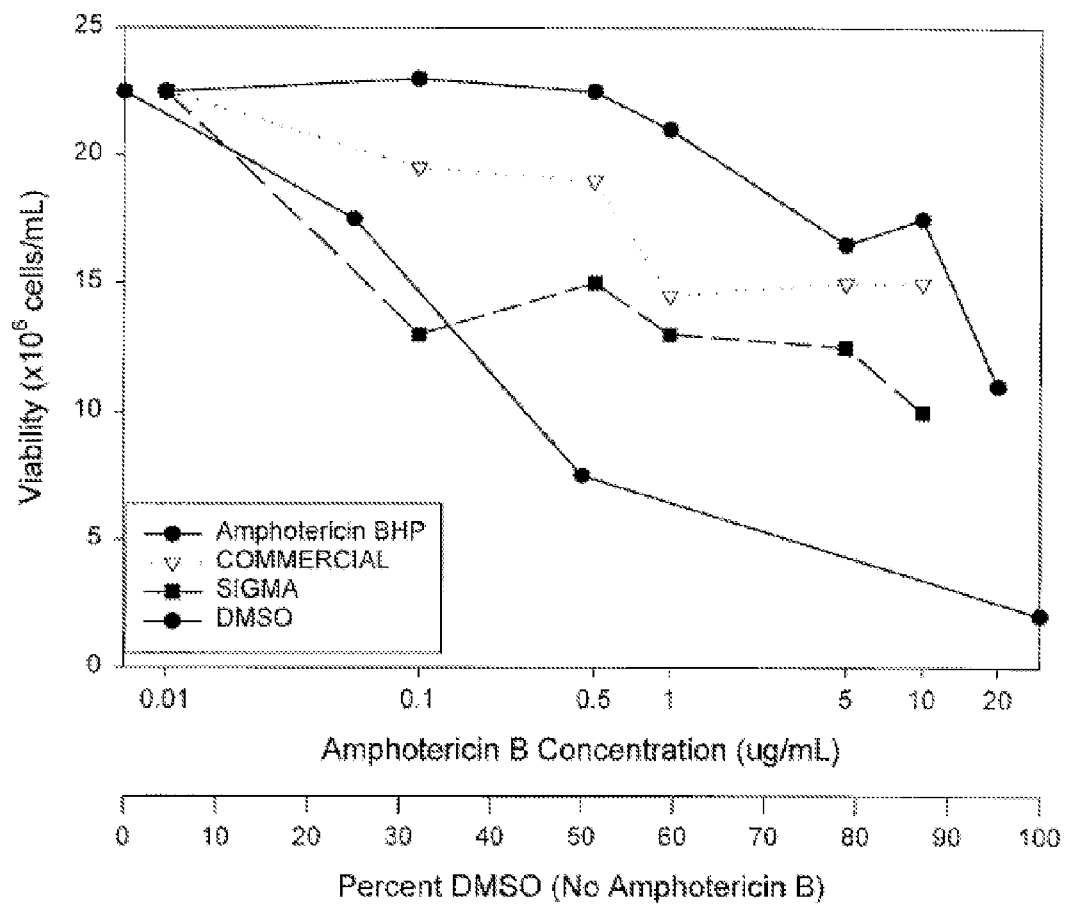
FIG. 2 is a graph that shows viability of AmBHP compared to AmB.

Viability Assay: Viability of cells is directly related to the quantity of DMSO used to solubilize AmBHP. Therefore, only concentrations less than about 6% are utilized. In addition, deoxycholate solution is used to solubilize AmBHP. Doxycholate did not cause decreases in viability compared to control at amounts less than about 20.2 mg per about 50 mg AmB. The viability of THP-1 cells exposed to AmBHP at concentrations ≤5 ug/mL is greater than the viability in cells exposed to the same concentrations of commercially available AmB or Sigma brand AmB (FIG. 2).

In vitro Infusion Related Reaction Assay: The potential of AmBHP and AmB to induce infusion-related reactions measured by IL-1β expression are displayed in FIG. 3 or 9. The amount of IL-1β expression associated with THP-1 cells exposed to the individual AmB formulations has been standardized to the Apothecon formulation and is represented as percent expression. Control cells exposed to sterile water or lipid express no more than about 120 pg/mL of IL-1β while Apothecon brand AmB cause the expression of about 300 pg/mL and 750 pg/mL IL-1β for the 0.1 ug/mL and 10.0 ug/mL concentrations, respectively. Less cytokine is expressed in response to AmBHP compared to the other formulations (Apothecon and Sigma). The difference is significant compared to Apothecon brand AmB.

AmB Assay:

Quantification of AmB in stock vials is completed within about 12 hours of the IL-1β. Apothecon brand AmB is measurable within about 5% of the reported values by the manufacturer. One concentration (5 ug/mL) of Sigma brand is measured at about 39.5±21.05 ug/mL. In addition, Sigma brand AmB is determined to be greater than about 5% of the manufacturers labeling in all samples tested. These data, suggest that there are several polyene antifungals in Sigma brand AmB which are identified by our AmB ELISA and that have spectrophotometric patterns distinct from AmB.

Spectrophotometric Assay: Quantitification of amphotericin A compound, AmB compound, and AmBHP is completed by spectrophotometry. Nystatin is used as the tetraene control representing amphotericin A and Apothecon brand as the standard for the hepatene AmB. The value obtained by utilizing Beer's Law (USP equation) to calculate amphotericin A compound should represent the amount of amphotericin A compound relative to the Apothecon brand AmB. No significant differences in amphotericin A or AmB compounds could be found in any of the AmB formulations utilized clinically (data not shown). Sigma brand AmB did contain significantly more of the amphotericin A compound in comparison to the commercial brands. Based on these spectrophotometric results, one could hypothesize that the AmB ELISA effectively measures polyene antifungals as a class. However, the presence of amphotericin A compound is not the complete explanation for the amphotericin measured in the ELISA. There are positive correlations between both AmB compound concentration and the concentrations of amphotericin A compound ($r^2=0.8831$; $p<0.01$) or interleukin-1β concentration ($r^2=0.9633$; $p<0.01$). AmBHP demonstrated a pattern consistent with other polyene antifungals.

Figure 5:
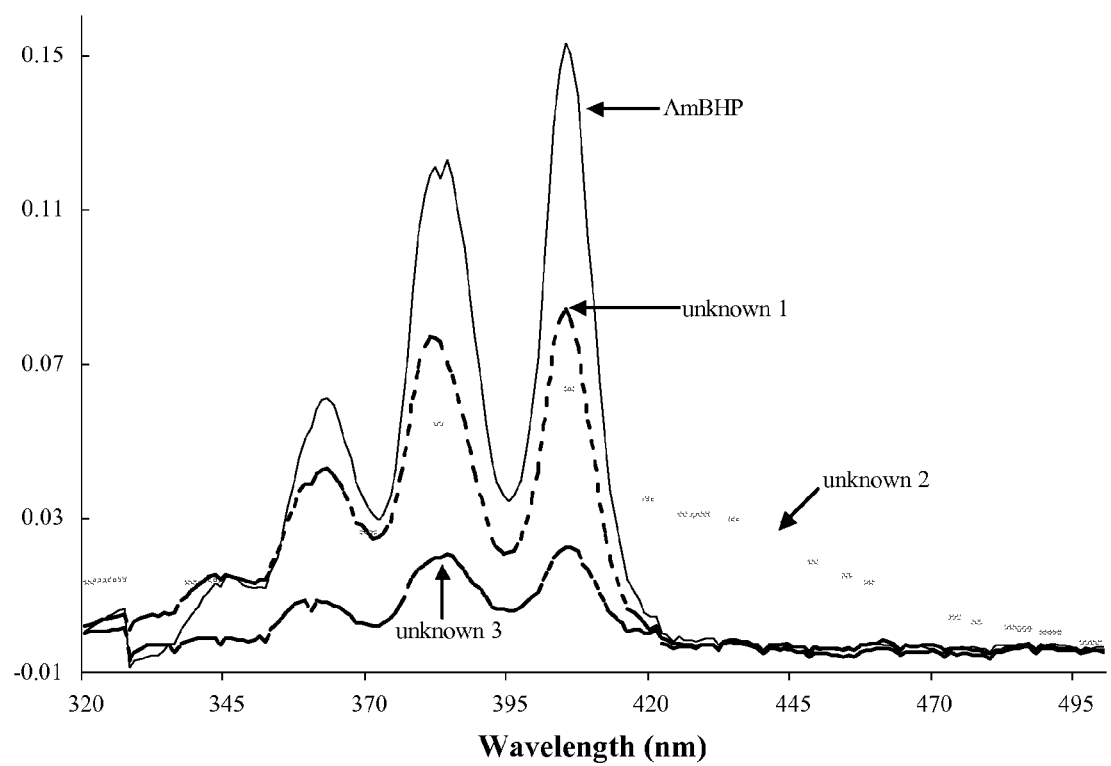
FIG. 5 shows absorbance spectra of high purity AmB (AmBHP) and other polyene components contained in generic AmB. An aliquot of Pharma-Tek AmB was subjected to semi-preparative HPLC and fractions corresponding to the AmB compound (i.e., AmBHP) as well as fractions containing peaks eluting before (unknowns 1 and 2) and after (unknown 3) the AmB compound were collected, and absorbance spectra of each fraction was then measured. Unknowns 1 and 2, respectively, correspond roughly with peaks eluting between 2-3 minutes and 5-6 minutes in the chromatograph shown in FIG. 1, whereas unknown 3 corresponds with the peak eluting between 9-10 minutes. Absorbance is expressed in Arbitrary Units.

Spectrophotometric evaluations of the unique absorption maximum for each of these polyenes, except for the hexaenes, are performed. The hexaenes share all spectrophotometric peaks with either a pentaene or a heptaene. Using Beers' Law, we calculated the amount of each polyene relative to Apothecon's product. Pentaene (unique O.D. peak=333) quantities are highest in the Sigma brand (about 167%) relative to Apothecon. Heptaene (unique O.D. peak=405) content is negligible (about <6.7%) in all except the Sigma Brand (about 10.8%). There are distinct peaks at optical densities of 345, 363 and 386 that correspond to either a pentaene or a hexaene. At these peaks (345, 363 and 386), differences in the products could be easily visualized (FIG. 5). The peak obtained at about 12 minutes is a polyene antifungal. The peaks that occur at other time points are also polyenes.

Bacterial endotoxin contamination could explain an increased observation of infusion related reactions when switching between products AmB manufactured by Lyphomed Pharmaceuticals in the early 1990s is identified as possibly contaminated. Therefore, we are diligent in testing our reagents for endotoxin contamination. Samples from diluent (sterile water), media, reagents and culture plates are assayed for endotoxin by the manufacturer utilizing the limulus amebocyte lysate. The limulus amebocyte lysate (LAL: Associates of Cape Cod Inc.; Woodshole, Mass.) testing employed an *Escherichia coli* endotoxin standard with a lower limit of detection of 3.0 pg/ml. AmB interferes with the LAL assay by disrupting the clot formation and clot adhesion, rendering this test difficult to perform and interpret. At concentrations achievable during clinical use, AmB interference appears to be minimal Testing of the Sigma brand and the Apothecon brand of AmB at 2.5 ug/mL and 5 ug/mL found no endotoxin.

Susceptibility Testing: DMSO inhibitory test. The results of the DMSO inhibitory tests displayed complete inhibition of growth at about 8% DMSO and partial inhibition at about 7%. The well with about 6% DMSO showed no visible difference from control. Therefore about 6% is set as the maximum allowable amount of DMSO in any well. Whenever possible, lower concentrations are used, but due to the limited sample sizes, levels near about 6% are often used in the well with the highest drug concentration.

Antifungal Susceptibility Testing:. Antifungal agents are prepared just prior to testing in all cases except in that of sample #1. After the addition of DMSO, it appeared that the drug had not completely solubilize. It is allowed to sit in the dark at room temperature for about 48 hours. The predetermined amount of RPMI is then added to the tube. An apparent exothermic reaction took place, releasing heat, and the remaining pellet dissolved completely. The sample is then used normally in susceptibility testing.

Other limitations are caused by the relatively small size of the sample drugs. Samples 2-7 are performed in duplicate and samples 1, 8-12 are performed in triplicate. These low concentrations also made it impossible to test the full range of drug concentrations for each sample. Samples 3 and 6 are only tested as high as 1 ug/ml and samples 2, 5, and 7 are tested up to about 2 ug/ml. Finally, as previously discussed, the sample size required higher concentrations of DMSO than normally utilized.

TABLE 3

Activity of HPLC fractions against *Candida albicans*[1]

| ELUTION TIME | Median $MIC_{80}$ | Median $MIC_{100}$ | $MFC^{1,2}$ |
|---|---|---|---|
| 1 | >4 | >4 | NT |
| 2 | 2 | >2 | NT |
| 3 | >1 | >1 | NT |
| 4 | >4 | >4 | NT |
| 5 | >2 | >2 | NT |
| 6 | >1 | >1 | NT |
| 7 | >2 | >2 | NT |
| 8 | 1.00 | 2 | 2 |
| 9 | 1.00 | 2 | 1 |
| 10 | 0.25 | 2 | 0.5 |
| 11 | 0.25 | 0.5 | 0.5 |
| 12 | 0.5 | 2 | 2 |
| Solvent | NA | NA % | NA |
| AmB | 0.10 | 0.25 | 0.625 |

[1]tested against *Candida albicans* B311
[2]tested against *Candida albicans* ATCC 90028 (NCCLS-recommended strain)
MIC = Concentration (μg/ml) that inhibits 80% growth
MFC = Concentration (μg/ml) that is fungicidal to all cells (no growth is seen on agar plates)
NT = not tried due to inactivity
NA = not active
AmB = AmB High Purity
Time = elapsed time in minutes.
MIC DATA RESPRESENT THE AVERAGE OF THREE TESTS Median susceptibility results are shown in Table 3. Results with a ">" sign signify that no inhibition is observed at or below these tested levels. Sample #2 displays a "2" for $MIC_{80}$ meaning that an 80% reduction is observed in this well. Though not indicated in the table, sample #2 causes some reduction at 2 ug/mL.

Example 2

This example shows AmBHP being isolated from commercially available AmB by semi-preparative reverse phase HPLC. Also shown are the effects of embodiments of the present invention compared in vitro and in vivo to those of commercially available AmB formulations.

As shown herein, AmBHP formulations of the present invention prove to be as efficacious as AmB formulations against *C. albicans* in vitro and as efficacious as both commercially available AmB and lipid-complexed AmB formulations in a *Candida*-infected mouse model AmBHP appeared to be less toxic to human THP-1 monocytic cells than was generic AmB at low concentrations (<2 μM), as indicated by exclusion of trypan blue and incorporation of [³H]thymidine. At higher concentrations, effects of AmBHP and Pharma-Tek AmB on thymidine incorporation and cytosolic calcium concentration were similar. General toxicity to AmBHP in vivo, as indicated by its apparent $LD_{50}$ and survival of *Candida*-infected mice, was roughly 2-fold less than was toxicity to generic or lipid-complexed AmB. Likewise, AmBHP decreased mean glomerular filtration rate about half as much as did a 10-fold greater dose of Pharma-Tek AmB.

This example shows that the present invention represents a refinement of currently marketed AmB formulations, offering equal, if not better, efficacy with less toxicity.

AmB Preparations: AmB formulations (Pharma-Tek® AmB: Pharmatek Laboratories, Inc.; San Diego, Calif.) was obtained as a lyophilized powder containing AmB, sodium deoxycholate and sodium phosphate, respectively, in ratios of 50:41:20.2 (mg:mg). Other AmB preparations formulated with deoxycholate were obtained through local distributors including: Apothecon brand AmB (Bristol-Myers Squibb, Princeton, N.J.), VHA brand AmB (repackaged Apothecon brand AmB), Sigma Chemical solubilized and nonsolubilized AmB (St. Louis, Mo.), United States Pharmacopea grade AmB (USP AmB: Alpharma ApS; Copenhagen S, Denmark) obtained as a non-solubilized formulation and lipid formulations of AmB (lipid complex: Enzon Pharmaecuticals, Bridgewater, N.J.; or liposomal: Astellas Pharmaecuticals, Deerfield, Ill.).

To obtain AmBHP, semi-preparative HPLC was performed by applying aliquots of commercially available AmB reconstituted in HPLC-grade water to a 10 mm (I.D.)×250 mm 5 micron AquaC18™ column (Phenomenex U.S.A.; Torrance, Calif.) and resolved with a gradient of methanol and 5 mM sodium phosphate (pH 5) at a flow rate of 1.5 mL/minute. Elution was isocratic with 75% methanol:25% phosphate buffer for the first 44 minutes, followed sequentially by a linear gradient to 85% methanol:15% buffer over 6 minutes and then isocratic elution for another 40 minutes. All ratios are expressed as vol:vol. Components of interest were cleared of salt, after evaporation of the methanol, by concentration in a solid phase matrix (e.g., C18) and washing with 10 volumes of HPLC-grade water. Solutes were next eluted with methanol, methanol was evaporated, and solutes were stored at 4° C. Immediately before use, solute (AmBHP) were dissolved in a minimal volume of DMSO and then diluted with 15 mM phosphate buffer (pH 7.4) containing 4.1 mg/mL sodium deoxycholate. The nominal purity of AmBHP was defined before isolation to be 95%. In practice, apparent purity of AmBHP varied between preparations from 96-99%. Estimates of purity are based on absorbance at 405 nm following resolution on a 4.5×150 mm AquaC18 column during isocratic elution with 70% methanol:30% 5 mM phosphate buffer (pH 5) at a flow rate of 1.2 mL/min.

Spectrophotometric classification of Pharma-Tek® AmB, AmBHP and other components resolved by HPLC was performed on the basis of ultraviolet absorption. The ultraviolet spectra for tetraenes (nystatin, amphotericin A compound) have characteristic peaks at 290 nm, 305 nm and 318 nm, whereas those for heptaenes (AmB compound) occur at 360 nm, 378 nm and 405 nm. Pentaenes and hexaenes share peaks at other optical densities, making it difficult to use other absorbance maxima to exclude them. Final polyene concentrations between samples were estimated on the basis of absorbance at 405 nm.

Susceptibility of Yeast: All organisms, including *Candida albicans* (ATCC 90028 & 44858), were obtained from the American Type Culture Collection (ATCC; Manassas, Va.). Strain 44858 was used as the primary yeast in these studies, except where noted. Cultures (for immediate use in assays) of all organisms were stored on either agar slants or plates at 4° C. until needed. Long-term storage of *C. albicans* strains was accomplished via freezing cells in 10% glycerol/broth (Sabouraud Dextrose broth; Difco, Detroit, Mich.) at −80° C. Effects of dimethyl sulfoxide (DMSO) on minimum inhibitory concentration (MIC) were tested using NCCLS broth microdilution guidelines (17). A total of 100 μL of DMSO and RPMI were placed in the wells of a microdilution tray so that the final concentrations of DMSO in tested wells varied between 1 and 30% (vol:vol). Yeast inoculum was prepared as described for antifungal susceptibility testing, and 100 μL were added to each test well. Then, cultures were incubated in a humid, dark chamber for 48 hours at 35° C.

Stock solutions of each dehydrated HPLC fraction (~60 second eluent intervals) were prepared by dissolving powder in DSMO and then diluting with RPMI 1640 buffered to pH 7.0 with 0.165M morpholinepropanesulfonic acid (MOPS) (PML Microbiologicals, Wilsonville, Oreg.). Based on the above control studies, the final concentration of DMSO was such that the concentration in test solutions comprised less than 6% of the total solution composition. Concentrations of DMSO greater than 6% appear to negatively impact susceptibilities. Stock AmB solutions (200 μM) were serially-diluted, and duplicate aliquots transferred to 96-well flat-bottom microplates. *C. albicans* inocula were prepared by picking 1-3 colonies from previously prepared agar plates and resuspending them in 3 mL 0.9% saline. Microorganisms were diluted in broth [Sabouraud Dextrose and cation-adjusted Mueller-Hinton (Difco)] to afford final target inocula of $5.0 \times 10^3$ CFU/mL after addition to the samples in a final volume of 200 μL. Growth (saline only), solvent and blank (media only) controls were included on each test plate. A $MIC_{50}$ was determined for all fractions and the reference AmB (Pharma-Tek® AmB) A minimum fungicidal or bactericidal concentration (MFC/MFC) was determined for Pharma-Tek® AmB and AmBHP. The MIC was defined as the lowest test concentration that allowed no detectable growth. The MFC was defined as the lowest test concentration that killed 100% of the organism.

In Vitro Cellular Toxicity: Assessment of AmBHP cellular toxicity was performed in a cultured cell system using human THP-1 monocytic cells. Initial comparisons between Pharma-Tek® AmB and AmBHP were made on cell viability, cytokine release and calcium signaling. Concentration-response relationships were established for Pharma-Tek® AmB, USP-AmB and AmBHP over a range which included therapeutic concentrations (i.e., ≤5.4 μM).

THP-1 Monocytic Cells—

The human monocytic THP-1 cell line [ATCC 212] was obtained from American Type Culture Collection (ATCC: Rockville, Md.). Cells were routinely grown in RPMI-1640 medium supplemented with 10% fetal bovine serum, streptomycin (100 μg/mL) and penicillin (100 U/mL) at 37° C. under a humidified atmosphere of 5% $CO_2$ in air. In some instances, media were buffered (pH 7.4) with 25 mM Hepes (N-[2-hydroxyethyl]piperazine-N'-[2-ethanesulfonic acid]). That and other modification are indicated in the descriptions of specific experiments.

Cell viability: The ability of THP-1 (ATCC TIB 202) cells to exclude trypan blue, as followed by light microscopy using routine procedures, was used to provide an initial comparison of cytotoxicities to individual HPLC fractions, including the fraction designated AmBHP, relative to the cytotoxicity of Pharma-Tek® AmB and Sigma AmB. Subsequently, tritiated thymidine incorporation was used to assess cytotoxicities to Pharma-Tek® AmB, USP AmB and AmBHP.

Thymidine incorporation was assessed by incubating THP-1 cells growing in RPMI containing 10% fetal bovine serum, 25 mM Hepes with [$^3$H]thymidine (1 μCi/$10^6$ cells; 62.5 pmol/μCi) (Perkin Elmer, Boston, Mass.). Logarithmically dividing cells were collected by centrifugation and resuspended in RPMI containing 25 mM Hepes supplemented with 20% fetal bovine serum. Tritiated thymidine was added to the suspension, and cells were immediately aliquoted to replicate 48-well culture dishes ($2 \times 10^6$ cells/well) for incubation in the absence (control) or presence (0.25-20 μM) of AmBHP, Pharma-Tek® AmB or USP AmB. Pharma-Tek® AmB was dissolved initially in DMSO, whereas USP AmB and AmBHP were dissolved initially in DMSO containing 4.1 mg/mL deoxycholate, to yield 5 mg/mL (~5.41 mM) stock solutions in which AmB:deoxycholate was 5:4.1. An aliquot of each stock solution was added to serum free RPMI containing 25 mM Hepes to a concentration of 40 µM, and the latter were used to prepare sequential dilutions. Aliquots of AmB solutions were added to cell culture wells, and the final concentrations of AmB preparations were obtained by addition of an equal volume of cell suspension. Comparable dilutions of DMSO or deoxycholate, but without AmB, were prepared for incubation with control cells. After a 24 hour incubation, 100 µL aliquots of each suspension were collected on glass fiber filters, the filters were washed, and radioactivity on the filters was measured by liquid scintillation counting.

Cytokine release: THP-1 cells were resuspended to a final concentration of approximately $5 \times 10^6$ cells/mL in supplemented media (RPMI-1640, 10% autologous serum, 100 µg/mL streptomycin and 100 U/mL penicillin). One milliliter of mononuclear cells were seeded in Limbro 24-well plates and incubated for 24 hours at 37° C. in 5% $CO_2$ AmB formulations were added to Limbro 24-well plates at final concentrations of <20 µM, and cells were then incubated for 2 hours. Supernatants were collected from each well after three freeze-thaws cycles and stored at −80° C. until assayed. Samples were assayed for interleukin-1β (IL-1β) using an enzyme-linked immunosorbent assay (Cistron Biotechnology; Pine Brook, N.J.). Manufacturer's data indicate an assay sensitivity of 20.0 pg/mL and a specificity for IL-1β, with no cross-reactivity for IL-1β, IL-2, tumor necrosis factor-α or γ-interferon. Evaluations of assay precision demonstrated a coefficient of variation of 5.3% to 6.7% for intra-assay variability and 6.6% to 8.4% inter-assay variability.

Calcium signaling: Changes in cytosolic free calcium concentration ([Ca]c) caused by Pharma-Tek® AmB and AmBHP were made to compare their general mechanisms of intracellular signaling. Measurement of [Ca]c in THP-1 cells was based on the use of fluorescent dyes, and details of the method have been described previously (11,12,22). Briefly, THP-1 cells suspended in RPMI/25 mM Hepes medium containing 10 nM PMA (phorbol-12-myristate 13-acetate) were seeded to 16 mm×93 mm Leighton tissue culture tubes containing a 9 mm×35 mm glass cover slip. After cells had adhered to the coverslips (typically 36-48 h), each coverslip—with adherent cells—was superfused with phenol red-free Hank's Balanced Salt Solution (HBSS) containing 0.2 mg/mL bovine serum albumin and 10 mM Hepes (pH 7.4). Fluorescence at 510 nm at excitation wavelengths of 340 nm and 380 nm was measured to obtain values for autofluorescence at the excitation maxima, respectively, of the calcium-bound and calcium-free forms of furaPE3. Next, cells were incubated for 45-60 minutes in HBSS/Hepes buffer containing the acetoxymethyl ester of furaPE3 (2 µM) (Tef Labs, Austin, Tex.) added in DMSO (2 µl/ml). Finally, cells were again superfused with HBSS/10 mM Hepes buffer, and fluorescence at 510 nm was recorded continuously while the excitation wavelength alternated between 340 nm and 380 nm. Either Pharma-Tek® AmB or AmBHP was added to the superfusate to a final concentration of 5.14 µM. Fluorescence measurements were corrected for autofluorescences of cells and drug prior to calculation of [Ca]c (7).

In vivo renal & hemodynamic Assessment: Sprague-Dawley (Harlan Sprague Dawley) rats (224-249 g) were housed in a temperature-controlled room on a 12:12-h light-dark cycle and fed standard chow (Harlan Teklad; Madison, Wis.) and water ad libitum for a period of at least 1 week before surgical procedures and experimental treatment. All procedures and experimental designs were in accordance with the guidelines of the American Association for Accreditation of Laboratory Animal Care (AAALAC) and approved by the University of Mississippi Medical Center's Institutional Animal Care and Use Committee. Animals were anesthetized using isoflurane delivered by an anesthesia machine (Vaporizer for Forane Anesthetic: Ohio Medical Products, Madison, Wis.). A midline lower abdominal incision was made, and the bladder was cannulated with flare-tipped PE-90 tubing for urine collection. Catheters of heat-stretched PE-50 tubing were inserted into the left femoral artery and right femoral vein for blood sampling and blood pressure monitoring. After implantation, each catheter was filled with a 50:50 solution of heparin and saline and exteriorized at the back of the neck. All animals were instrumented with a specially made Silastic catheter and steel bladder as described by Gellai and Valtin for renal clearance measurements (5). On complete instrumentation, all animals were allowed to recover for a period of 4 days.

Initial pilot studies were performed to determine the "nephrotoxic dose" for Pharma-Tek® AmB. Doses studied for assessment of renal toxicity range started at 1 mg/kg as a single dose infused at 0.015 mL/min over 1 hour. Incremental increases in dose were performed until 2 mg/kg was achieved. That dose was deemed to be nephrotoxic on the basis of a 16% reduction in mean glomerular filtration rate (GFR). For all future studies, Pharma-Tek® AmB was administered at 2 mg/kg/hr for one hour. A dose for AmBHP and lipid AmB agents was arbitrarily selected at 10-fold this dose. In experimental studies, animals were treated with saline for up to 1 day and then placed in modified restraining cages for renal function measurements. Each animal served as their own control, prior to receiving AmB formulations. These animals were then crossed over into the treatment arm to receive Pharma-Tek® AmB 2 mg/kg/hr compared to AmBHP, AmB lipid complex or liposomal AmB at 20 mg/kg/hr. The femoral vein catheter was then connected to an infusion pump. Isotonic saline containing sodium [$^{125}$I]iothalamate and para-aminohippurate (PAH) was infused intravenously at a fixed rate of 3 mL/h After a 60-minute stabilization period, two 20-minute urine collections were obtained, followed by collection of blood samples. Urine volume was determined gravimetrically. Sodium and potassium concentrations in plasma and urine were measured by flame photometry. Glomerular filtration rate and effective renal plasma flow were calculated from the radioactivity of $^{125}$I and concentration of PAH, respectively, in plasma and urine. PAH concentration was determined colorimetrically. Arterial pressure was monitored in conscious animals with a pressure transducer connected to a Grass model 7B chart recorder for continuous recording. The arterial line was flushed with saline and connected to a pressure transducer (Cobe III Transducer CDX Sema, Birmingham, Ala.).

Survival in an Infection Model: Evaluation of efficacy was performed in a murine *Candida albicans* systemic infection model. For each experiment, an isolate of *C. albicans* ATCC 44858 was thawed and then incubated overnight on Sabouraud dextrose agar (Unipath Limited). One colony was transferred into 25 mL of Sabouraud dextrose broth (Unipath Limited). The broth was incubated on an orbital mixer for 8 hours at 37° C., centrifuged to pellet the organisms, and then washed and resuspended in saline. Density was adjusted using optical density at 490 nm. Initial studies were performed in which 0.15-0.2 mL saline containing this *Candida* strain over a range of densities was injected intravenously to determine the optimum inoculum. The 90% lethal dose ($LD_{90}$) was defined as the inoculum of the organism that caused 90% mortality 10 days post-infection. The inocula for the all isolates are estimated at 3-5×10$^8$ CFU/mL. These inocula were used in this study.

A preliminary study also was performed to identify an appropriate dose of AmB and AmBHP. Increasing doses (1-15 mg/kg) of Pharma-Tek® AmB were administered to fasting uninfected Balb/c mice over 2 minutes. At doses of 2 mg/kg (N=4) or less, no overt toxicity was observed. However, at doses of 3 mg/kg (n=8) and 4 mg/kg (n=5), respectively, 80% and 100% of the animals succumbed. Since these data indicated an LD$_{50}$ of 2-3 mg/kg, Pharma-Tek® AmB was not used at doses greater than 2 mg/kg. In contrast, an LD$_{50}$ was not reached for AmBHP or for the lipid formulations of AmB at doses up to 5 mg/kg.

Specific-pathogen-free Balb/c mice (age 12-20 weeks) were obtained from IFFA Credo (L'Arbresle, France). Female mice were infected with 0.15-0.2 mL of *C. albicans* inoculum (4×10$^8$ CFU/mL) by injection into the lateral tail vein and then returned to their home cages. Post-infection viability counts were performed to ensure the correct inoculum had been given. Mice were treated after 16 hours with a starting dose of 0.5 mg/kg of a non-lipid AmB formulation or 5 mg/kg of a lipid formulation. At time of death or animal sacrifice, vital organs (liver, spleen, heart, bladder, muscle) were isolated and transferred into 2 mL cold sterile phosphate-buffered saline. Samples were frozen at −80° C. until analysis. At batch processing time, each sample was thawed and weighed. The organs were divided into 2 batches. Organs in one batch were homogenized in a tissue grinder for 14-30 seconds and then diluted 1:10, 1:100, and 1:1000. A 100 µL aliquot of each sample was plated on Sabourauds dextrous agar and incubated at 37° in a humidified incubator. Plates were examined daily for 7 days, and colony counts were recorded from all plates each day. The second batch of organ tissue was evaluated microscopically. Leukopenia was not induced by intraperitoneal administration of cyclophosphamide at 100 mg/kg 4 days before *C. albicans* inoculation due to the overall success of the model and the desire to maintain competency of the immune system.

Statistical Analysis: Animal survival between treated and untreated infected animals was selected as the primary outcome measure. These data were analyzed using Log-rank analysis. All other data are presented solely as demonstrative characterizations.

Figure 4:
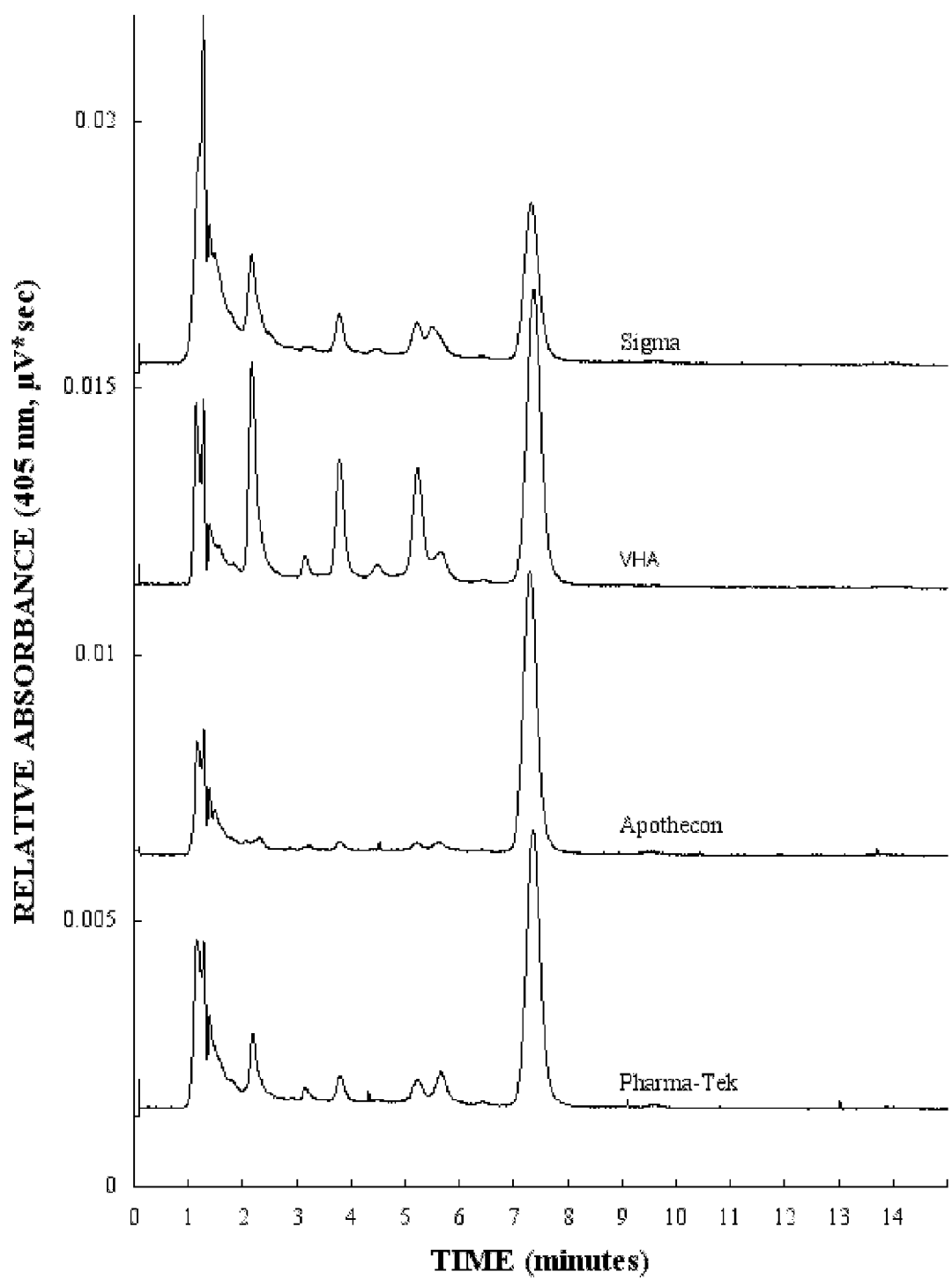
FIG. 4 is a chromatograph that shows a comparison of commercially available deoxycholate-based formulations of AmB. Components of Sigma Chemical grade AmB (Sigma), Apothecon brand AmB (Apothecon), repackaged Apothecon brand AmB (VHA) and Pharma-Tek brand AmB (Pharma-Tek) were resolved by HPLC and detected by absorbance at 405 nm. All chromatographs are presented on the same scale, but baselines have been off-set to allow distinction of individual samples.
Figure 6:
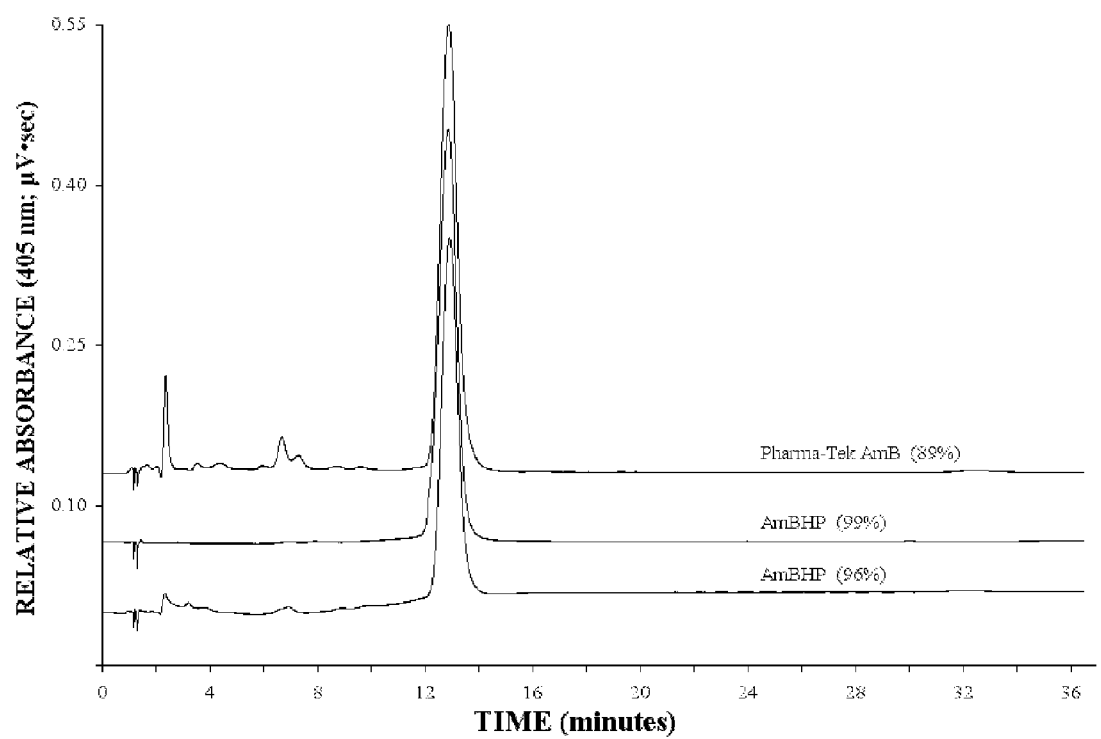
FIG. 6 shows chromatographic comparison of Pharma-Tek AmB and AmBHP. Aliquots of Pharma-Tek AmB and two separate preparations of AmBHP were subjected to HPLC, and absorbance of the eluates were monitored at 405 nm. The absorbance scale is the same for all AmB preparations, but baselines have been off-set to separate individual chromatographs. Apparent purities are indicated in parenthesis.

Results: Analytical HPLC demonstrated the presence of multiple components in a number of commercially available AmB formulations (FIG. 4 or 6). Although the chromatographs are qualitatively similar, there are considerable quantitative differences in the amounts of individual components. In fact, the amount of AmB compound, as indicated by absorbance at 405 nm, accounted for only 50% (VHA AmB) to 90% (Apothecon AmB) of the material present in AmB. Sodium deoxycholate, which is added as a surfactant to non-lipid commercial formulations, had no detectable absorbance at 405 nm. Thus, it makes no contribution to the estimate of relative purity. UV/VIS absorbance spectroscopy of fractions corresponding to AmB compositions (and compositions of the present invention) as well as fractions corresponding to some earlier- and later-eluting peaks resolved by semi-preparative HPLC indicate that most of the components absorbing at 405 nm are polyene in nature (FIG. 5). All polyenes exhibited characteristic absorbance maxima near 365, 380 and 405 nm. A quantitative comparison of amphotericin A compound (AmA), AmB, and AmBHP was completed by absorbance spectrophotometry. Nystatin was used as the tetraene control, representing AmA, and Apothecon brand AmB was the standard for the heptaene. There were distinct peaks at optical densities of 345, 363 and 386 that correspond to either a pentaene or a hexaene in all AmB samples. Pentaene (unique O.D. peak=333) quantities were highest in Sigma AmB (10.8%), and negligible (<6.7%) in the other AmB samples. The maximum in absorbance at 405 nm, together with additional absorbance peaks at 385, 363 and 345 nm, are consistent with AmBHP being a heptaene AmBHP used in the studies reported here had a purity of 95% or greater (FIG. 5). That level of purity represents a significant improvement over currently available non-lipid AmB such as Pharma-Tek® AmB (apparent purity of ~89%) and possibly the AmB used for lipid formulation.

Initial studies were performed to test the relative properties of the various polyene components in Pharma-Tek® brand AmB which were resolved by analytical reverse phase HPLC. In these experiments, column eluate was collected in 1 minute fractions, with no attempt to pool fractions corresponding to individual peaks in the chromatograph. AmBHP eluted as a single peak between 7 and 8 minutes, corresponding to fraction 8. Eluted samples were dried under nitrogen and reconstituted in DMSO just prior to testing against *C. albicans*. To the extent possible, DMSO concentration (vol:vol) was maintained <6%, the maximal concentration that showed no visible difference from control susceptibility studies. Heptaene content of each fraction was estimated by absorbance at 405 nm. Samples were run in duplicate and at multiple concentrations when possible. Minimum inhibitory concentrations indicate that fractions corresponding to AmBHP as well as fractions eluting immediately before and after the AmB compound had activity against the ATCC strain of *C. albicans* tested. The greatest activity was exhibited by fraction 8, corresponding to AmBHP, which had an MIC$_{80}$ of 0.25 µM and an MFC of 0.5 µM. Fractions 6 and 7, which eluted immediately before AmBHP, each had an MIC$_{80}$ of 1 µM, whereas the MFC for fractions 6 and 7, respectively, were 2 µM and 1 µM. Fractions containing earlier eluting polyenes were not tested for MFC, but each had an MIC$_{80}$ greater than 1 µM. The MIC$_{80}$ was >1 µM for fractions 2 and 4, and it was >2 µM for the remaining fractions. Finally, fraction 10, which eluted after AmBHP, exhibited an MIC$_{80}$ and an MFC, respectively, of 0.5 µM and 2 µM. Clearly, AmBHP had superior inhibitory and cidal activities compared to fractions containing other polyene components.

Figure 7:
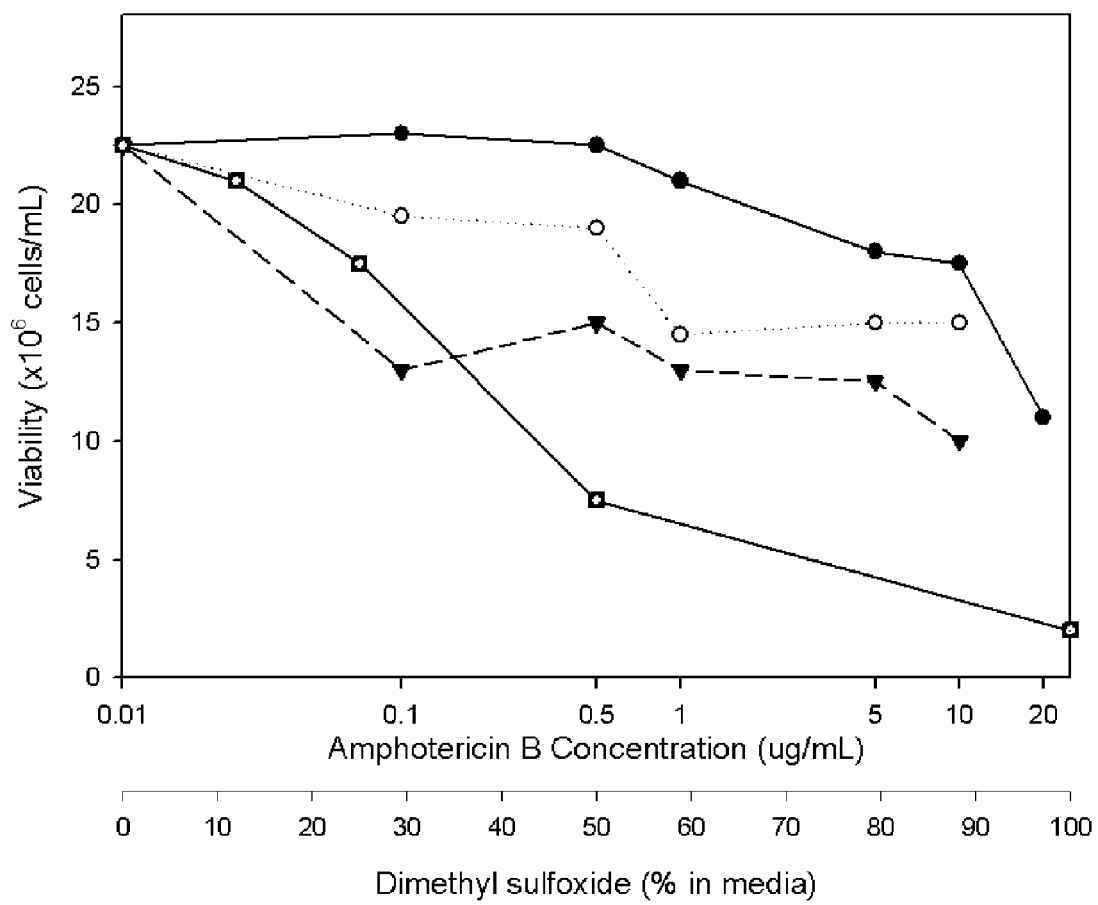
FIG. 7 is a graph that shows cell viability as determined by visual microscopic inspection using trypan blue exclusion. Values represent the mean of triplicate sample assessments performed on the same day. Conditions include: ▼—Sigma brand AmB, ○—Generic (PharmaTek) brand AmB, •—AmBHP on the top abscissa and ▲—Dimethyl sulfoxide on the bottom abscissa.
Figure 8:
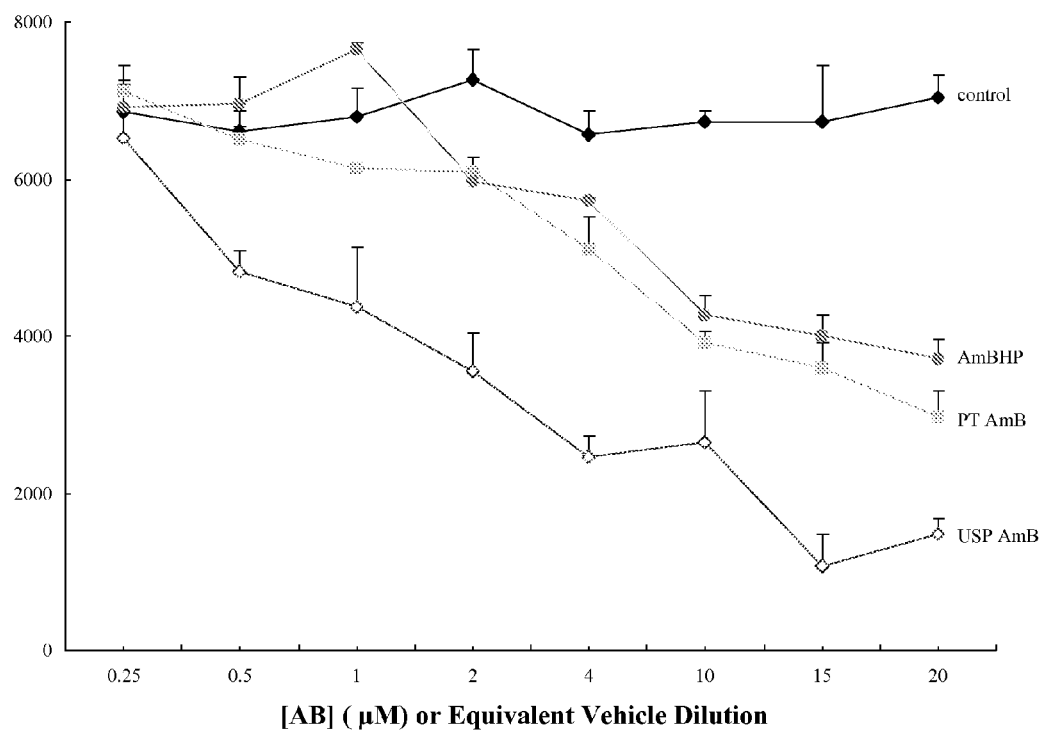
FIG. 8 is a graph that shows cell viability as determined by the effects of AmBHP Pharma-Tek® AmB (PT AmB) and USP AmB on thymidine incorporation by THP-1 cells. Incorporation of [$^3$H]thymidine by THP-1 monocytic cells incubated in the absence (control, ♦) or presence of increasing concentrations (0.25-20 µM) of USP grade AmB (USP AmB, ◇), Pharma-Tek brand AmB (Pharma-Tek, ■) or AmBHP (●) was assayed over a 24 h period. Data are expressed as mean±SEM (n=3) of three separate experiments in which each condition was replicated twice.

Toxicity of AmBHP and other polyenes present in AmB in fractions resolved by analytical HPLC were evaluated initially on the ability of THP-1 cells to exclude trypan blue (FIG. 2 or 7). Samples dissolved in DMSO (<6%, vol:vol) or sodium deoxycholate did not affect cell viability at concentrations ≤10 µM. Thus, on the basis of trypan blue exclusion, AmBHP appears to be less disruptive to the cell membrane than is commercial deoxycholate-formulated AmB. Concentrations greater than 5.4 µM (~5 µg/mL) of the latter are well recognized to induce cellular toxicity. To refine our understanding of the relative cellular toxicity of AmBHP a comparison was made between it and AmB formulations using incorporation of [$^3$H]thymidine as an index of cytoxicity. Incorporation of [$^3$H]thymidine differentiates cell death from loss of viability since it measures the synthesis of new DNA. All three AmB preparations tested caused concentration-dependent reductions in [$^3$H]thymidine incorporation Inhibition by AmBHP or Pharma-Tek® AmB was less pronounced than was inhibition by USP AmB. Likewise, inhibition of thymidine incorporation was apparent at a lower concentration of Pharma-Tek® AmB than AmBHP. However, at higher concentrations (≥2 µM), the effects of AmBHP and Pharma-Tek® AmB were indistinguishable (FIG. 8). Sigma brand AmB was not used in thymidine assessments due to its overall toxicity observed with trypan blue.

Figure 3:
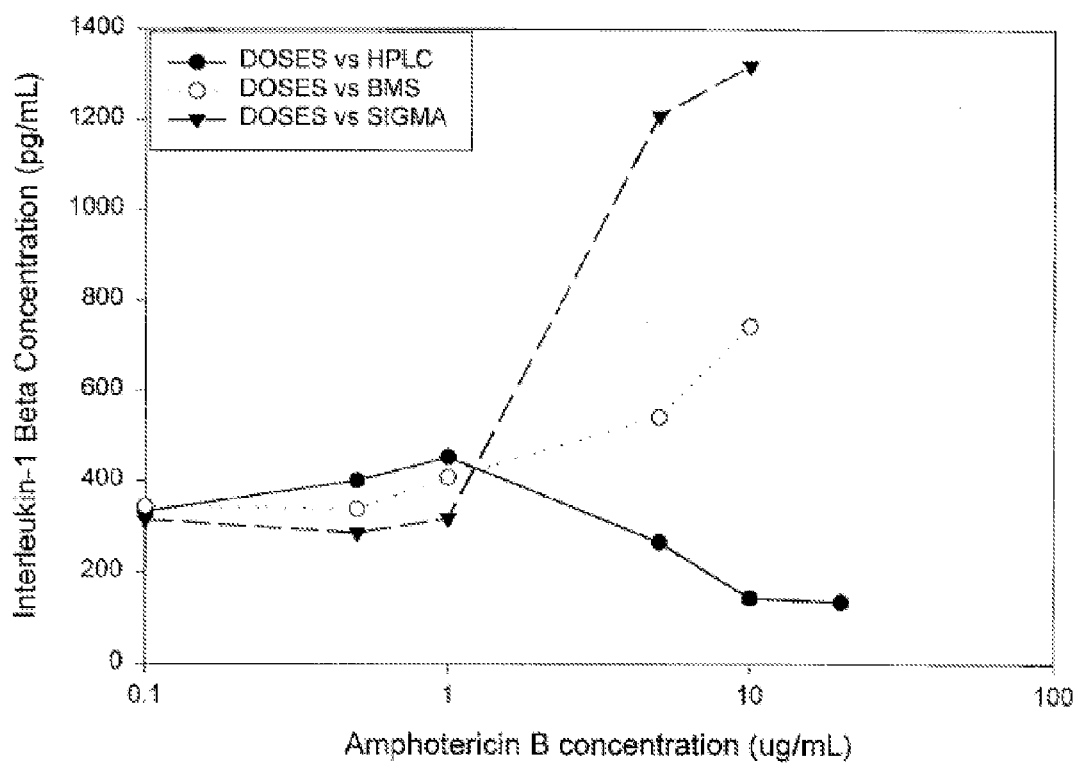
FIG. 3 is a graph that shows cytokine response induced by AmBHP compared to AmB.
Figure 9:
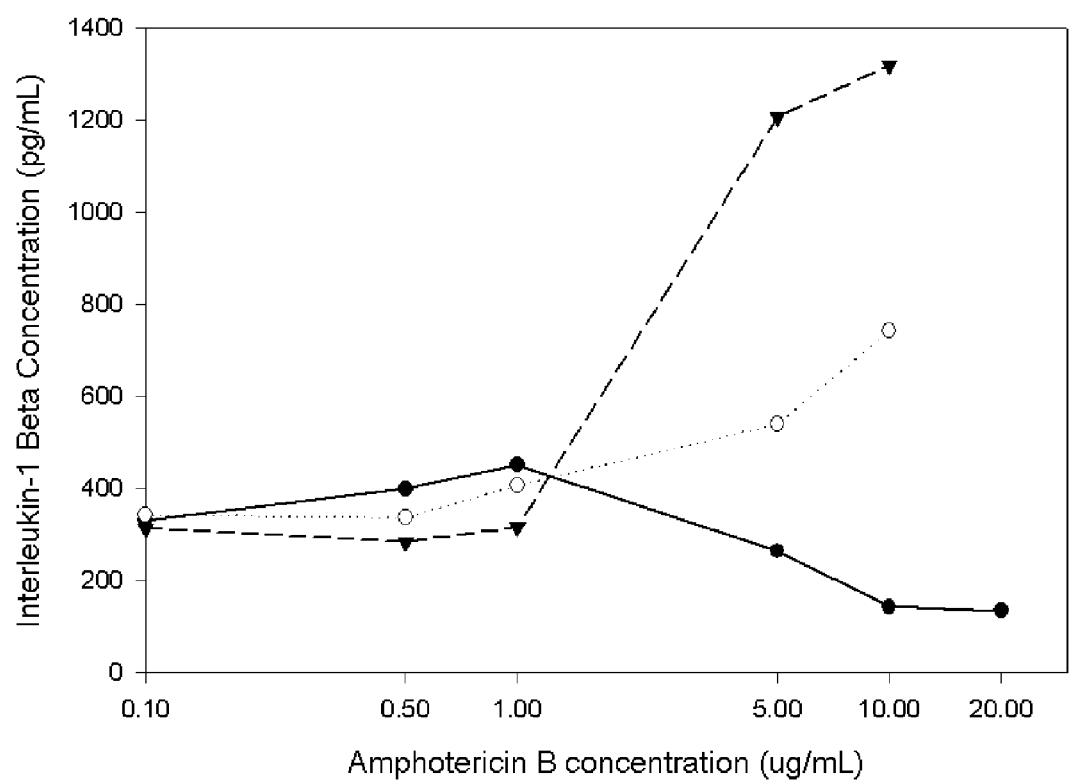
FIG. 9 is a graph summarizing a cytokine release assay. This assay can predict infusion related reactions associated with AmB formulation administration in man. THP-1 (mononuclear like) exposed to varying concentrations of AmB formulations (▼—Sigma brand AmB, ○—Generic (PharmaTek) brand AmB, •—AmBHP) release a pro-inflammatory cytokine which may be used as a marker for toxicity.

The potential for AmB formulations to induce infusion-related reactions can be assessed in vitro by their ability to promote the release of cytokines such as interleukin-1β (IL-1β). Control THP-1 cells incubated in the absence of AmB expressed no more than 120 pg/mL (7.1 fmol/$10^6$ cells/24 h) of IL-1β, whereas the expression of IL-1β increased to 300 pg/mL (17.6 fmol/$10^6$ cells/24 h) and 750 pg/mL (44.1 fmol/$10^6$ cells/24 h), respectively, in response to 0.1 μg/mL (0.11 μM) and 10.0 μg/mL (10.82 μM) Pharma-Tek® AmB (FIG. 3 or 9). Chemical grade AmB (Sigma AmB) caused substantially greater expression of IL-1β at concentrations greater than 1 μg/mL (1.08 μM) than did Pharma-Tek® AmB. In contrast, AmBHP caused less of a cytokine response than did AmB. Although AmBHP increased IL-1β expression to rates comparable to those achieved in response to Pharma-Tek® AmB and Sigma AmB at concentrations ≤1.08 μM, AmBHP failed to further increase cytokine release at concentrations as high as 21.6 μM. Cell counts at the end of each study demonstrated no differences in cell growth or mortality between groups.

Figure 10:
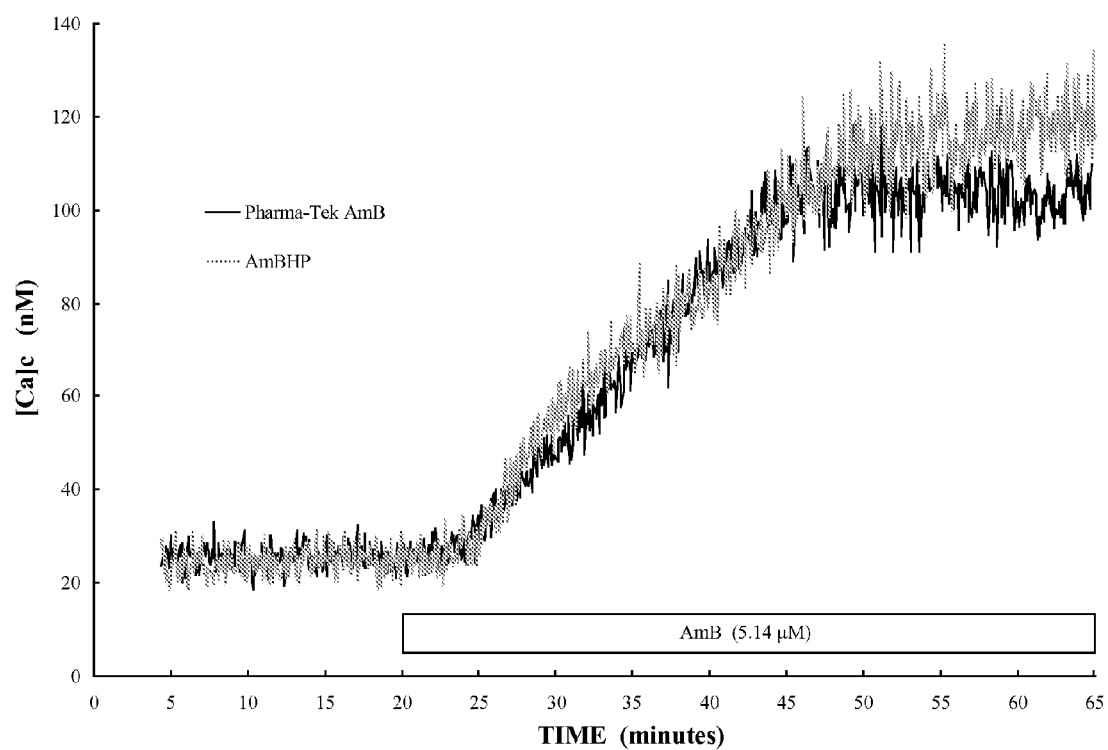
FIG. 10 shows calcium signaling. The effects of AmBHP and Pharma-Tek® AmB (PT AmB) on cytosolic free calcium concentration in THP-1 cells.
Figure 11:
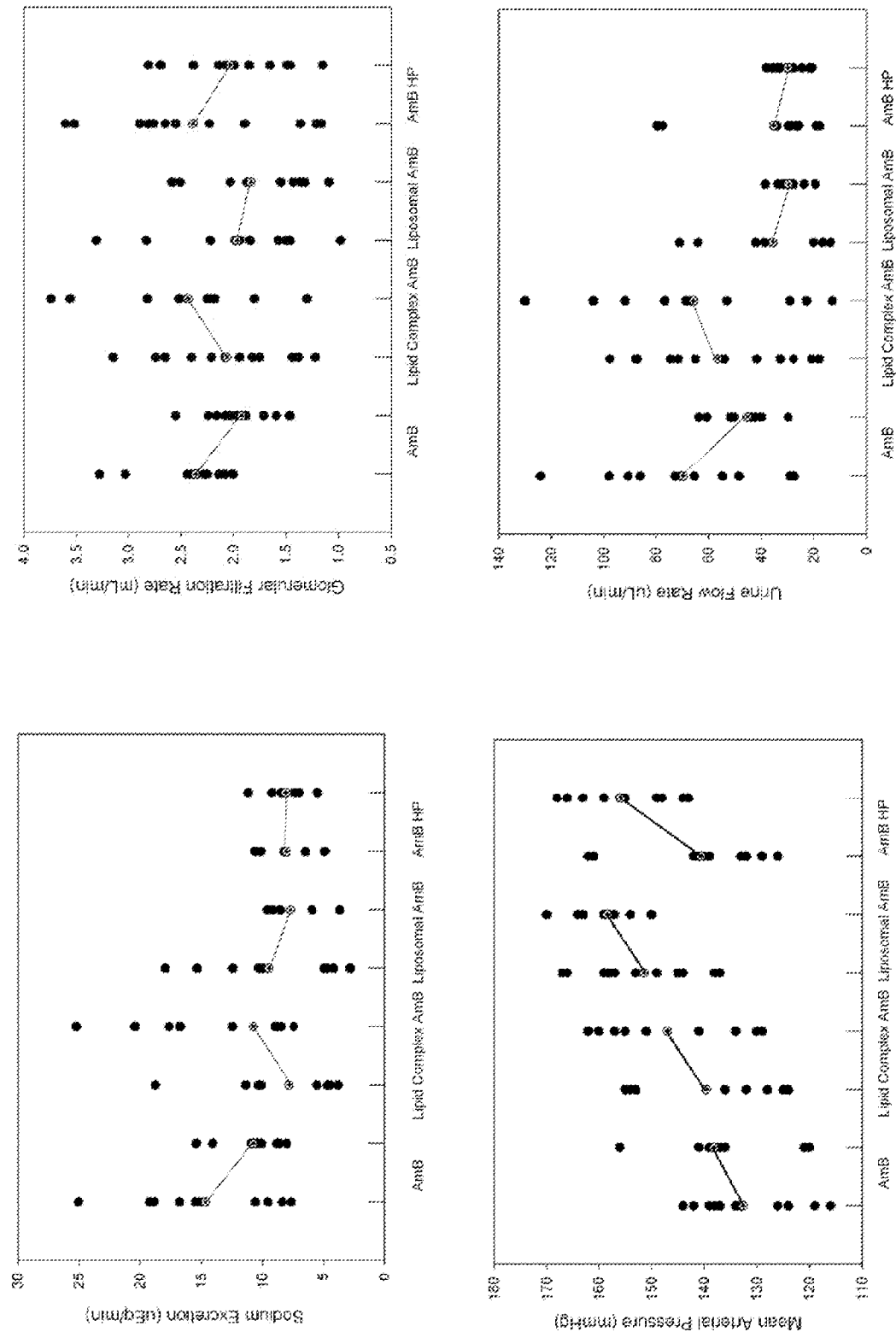
FIG. 11 summarizes renal function studies. Rats were administered single doses of AmB 2 mg/kg, or lipid complex AmB, liposomal AmB and AmBHP 20 mg/kg over one hour. All animals entered into a match design, where saline was administered and renal function was assessed. After baseline was established, the AmB and AmBHP formulations were administered in groups of 5 animals.

The present inventors have demonstrated previously that the increase in IL-1β expression by THP-1 cells caused by Pharma-Tek® AmB is accompanied by an increase in [Ca]c (22). Since the calcium signal in response to AmB might be as much an index of cytotoxicity as it is a reflection of intracellular signaling for pro-inflammatory cytokine release, studies were performed to compare the changes in [Ca]c caused by Pharma-Tek® AmB with those caused by AmBHP. Not surprisingly, the data indicate that an increase in [Ca]c likely contributes to the effects of both Pharma-Tek® AmB and AmBHP on cell function. It is also noteworthy that the calcium signals elicited by AmB and AmBHP were similar in magnitude and kinetics (FIG. 10). In light of the difference in apparent purities of the particular AmBHP (98%) and Pharma-Tek® AmB (88%) used in this set of experiments, the similarities in the calcium signals suggest that an increase in [Ca]c may be a common action of all the polyenes components in the latter preparation. USP AmB elicited a calcium signal that was comparable to those caused by AmBHP and Pharma-Tek® AmB (data not shown).

Figure 12:
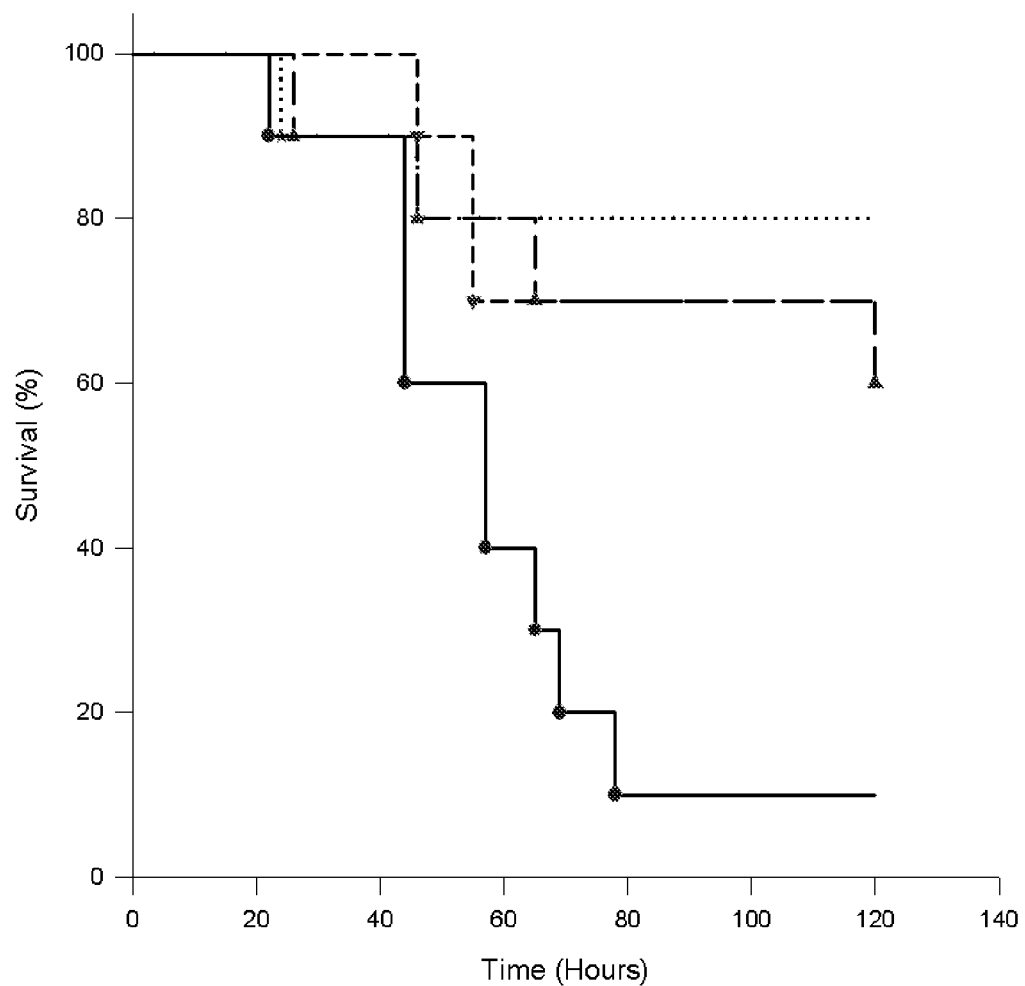
FIG. 12 summarizes survival studies in disseminated candidiasis. Survival [LogRank] analysis was performed for animals (N=5) receiving each AmB and AmBHP formulation or control saline in our murine candidemia model. Each exposure is labeled: —— Saline, ——— ABLC, ······ AmBHP, — — AmB DOC. Survival was superior in all three treatment groups compared to control (p<0.01). None of the treatment groups were statistically different in outcome. Generic AmB (Pharma-Tek® AmB: Pharmatek Laboratories, Inc.; San Diego, Calif.) were obtained as a lyophilized powder containing AmB, sodium deoxycholate and sodium phosphate, respectively, in ratios of 50:41:20.2 (mg:mg). Other AmB formulations with deoxycholate were obtained through local distributors including AmB (Bristol-Myers Squibb, Princeton, N.J.), VHA brand AmB (repackaged Apothecon brand AmB), Sigma Chemical.

Renal toxicity associated with AmB and AmBHP varied. The doses were initially titrated to identify one that was associated with overall acute renal toxicity in vivo (2 mg/kg), yet not be associated with acute lethality (>2 mg/kg). The final doses selected were 2 mg/kg for Pharma-Tek® AmB and 20 mg/kg for both the AmB lipid formulations and AmBHP, each administered for one hour. When data are viewed as percent control, one can easily notice the differences in renal function (GFR) of animals treated with AmBHP (7.9% decrease) or liposomal AmB (16.4% decrease) compared to the renal function of animals treated with Pharma-Tek generic AmB (12.3% decrease). The increase in renal function observed with lipid complex AmB (10.9% increase) was also associated with increased sodium excretion and urine flow rate, suggesting an increase in renal blood flow. Glomerular filtration rates (GFR) for control animals varied between 1.96 and 2.37 mL/min (mean=2.19 mL/min) The mean GFRs of animals treated with AmBHP (2.03 mL/min), amphotericin lipid complex (2.43 mL/min), liposomal AmB (1.83 mL/min), and AmB (1.92 mL/min) were comparable to the mean GFR for control animals. It is also noteworthy that other indices of cardio-renal function were not adversely affected by AmBHP at doses well outside (10-fold) the range of toxicity for AmB in vivo. In fact, they compared favorably with values noted in animals treated with lipid formulations of AmB (FIG. 12).

Efficacy of Pharma-Tek® brand AmB (0.5 mg/kg), AmBHP (0.5 mg/kg) and AmB lipid complex (AmBLC; 5 mg/kg) was assessed after *C. albicans* inoculation by monitoring mortality for a maximum of 5 days post infection. In initial studies, five (5) sets of uninfected animals have completed dose-ranging tests. Data obtained from 5 sets of mice indicate that the $LD_{50}$ for AmBHP (~5 mg/kg) is at least twice that of commercial AmB (~2.5 mg/kg) (data not shown). At 5 days post infection, mortality from disseminated candidiasis in animals not treated with AmB was 90%. As illustrated in FIG. 12, any treatment was significantly better than no treatment (p<0.01). Even though survival between the 3 treatment groups was not statistically different, AmBHP appeared to have the greatest efficacy. Mortality in infected mice treated with AmBHP was only 20%, whereas mortality in animals treated with either Pharma-Tek® AmB or AmBLC was 40%.

Importantly, despite the lack of a statistically significant difference, a clear trend towards improved survival is observed with AmBHP in infected animals. That trend is potentially even more important in as much as AmBLC was given at a 10-fold greater dose. In any event, these data and data related to nephrotoxicity suggest that formulation of AmBHP with a lipid carrier would further improve both efficacy and safety in vivo.

The *C. albicans* tissue burden following treatment of infected mice with AmB or AmBHP provided another assessment of relative efficacy. In general, results of post-mortem examinations of liver, spleen, heart, kidney, lung and blood indicate that the efficacy of AmBHP is comparable to those of Pharma-Tek® AmB and AmBLC. Although no statistical analysis was planned or performed due to the small sample size, lower colony counts from lungs and livers of AmBHP-treated animals suggest that it might be more efficacious in those tissues than is AmB. Likewise, AmBLC appeared to have the greatest activity of the three AmB formulations against fungi in blood, from which no colonies were observed from AmBLC-treated animals in repeated studies. Even so, AmBHP was as effective against blood-borne fungi as was Pharma-Tek AmB.

Example 3

This example demonstrates additional methods of making examples of the present invention. The column used may be a CN HPLC column, including, for example, a phenomenex axial pack 21.2×250 mm CN column; 10 micron particles; 100 angstrom pore size. The column may be washed with ethanol:1 N HCl (99:1; vol:vol; if in water pH ~2) and then equilibrated with 70:30 (ethanol:phosphate buffer pH 5) before a given series of preparative runs. The solvent is ethanol:5 mM phosphate (pH 5); 70:30 (vol:vol). The column flow is 1.0 mL/min from 0-65 minutes; linear increase to 3.0 mL/min by 67 minutes; and 3.0 mL/min until 180 minutes. The column pressure is less than 2000 psi. The solvents and column are at ambient temperature.

The fractions are collected at 5 minute intervals; fraction volume between 1 and 65 minutes is 5 mL, whereas it is 15 mL after 70 minutes.

The absorbance of column effluent is monitored at 363 nm. That measurement is coupled with measurement of the absorbance of an aliquot of each fraction at 405 nm if peaks can not be visualized.

The AmB used in this example is USP grade (Alpharma). For this example shown, 110 mg USP AmB were dissolved in 2 mL DMSO, and 600 μL (~33 mg) were injected in each of a series of three consecutive runs, with the results of one run illustrated. The amphotericin B:DMSO solution is freshly prepared and kept at 0-4° C. between runs.

Figure 13:
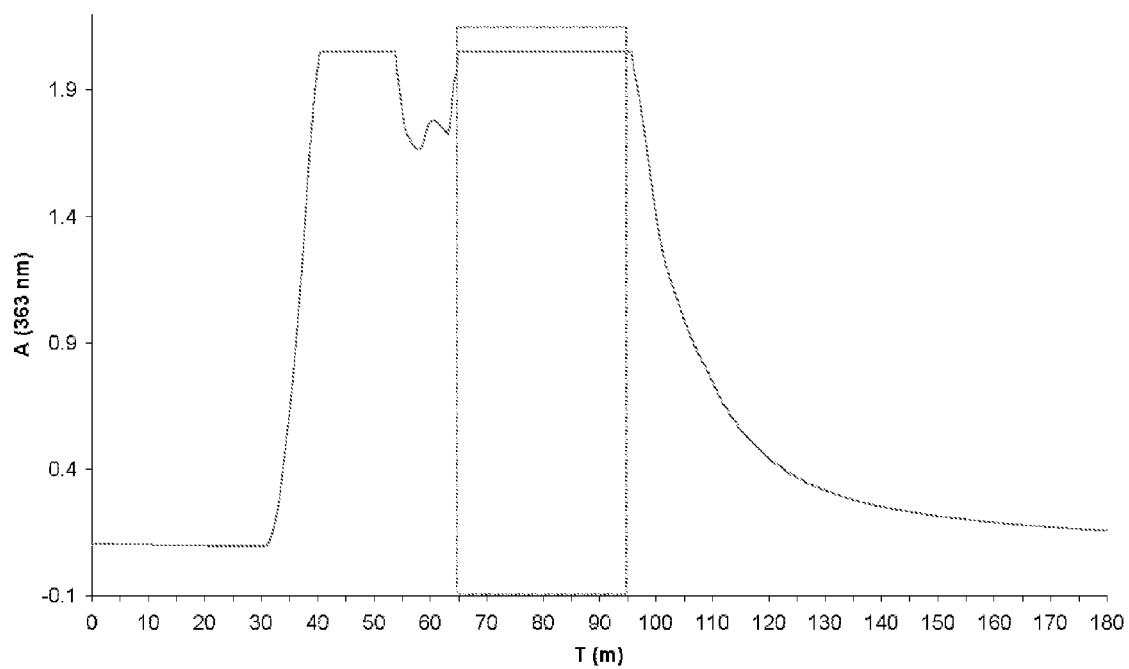
FIG. 13 is a chromatogram that shows absorbance of column effluent of an embodiment of the present invention monitored at 363 nm.
Figure 14:
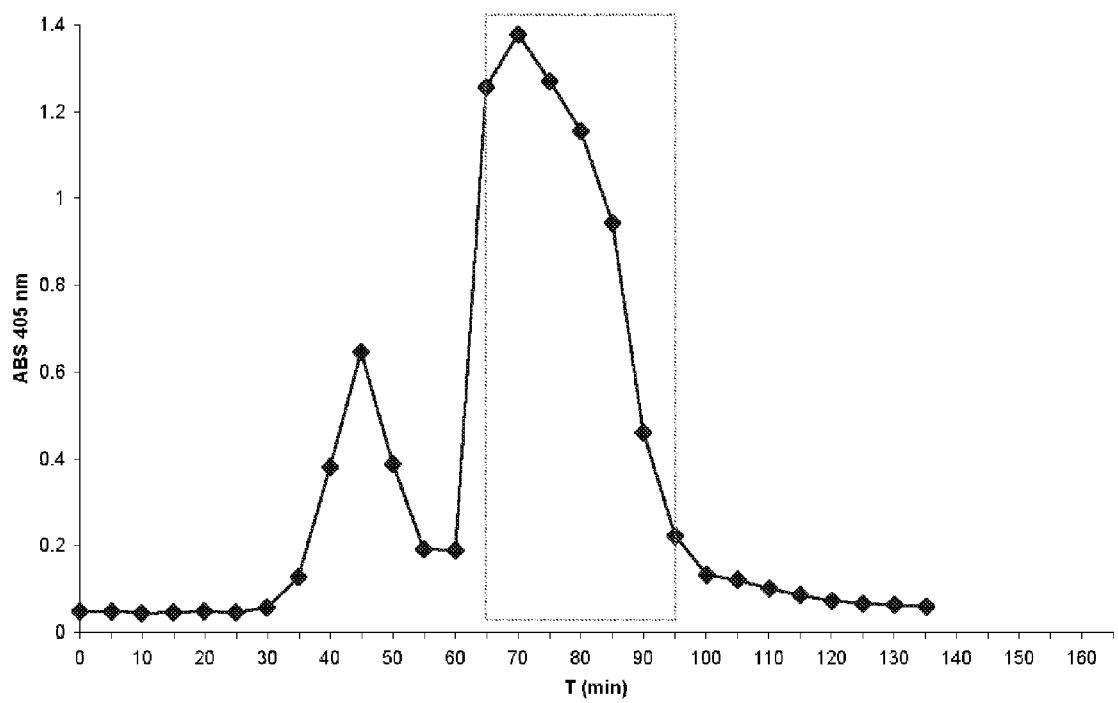
FIG. 14 is a chromatogram showing absorbance of corresponding fractions measured at 405 nm.

See FIG. 13, a chromatogram obtained using a method of this example (absorbance of column effluent monitored at 363 nm). Additionally, FIG. 14 shows a chromatogram (absorbance of corresponding fractions measured at 405 nm).

Appropriate fractions are pooled (fractions 14-19 and as indicated by the dotted box), the volume is estimated, and the pooled sample is diluted with one half volume of cold (0-4° C.) 10 mM phosphate buffer (pH 7-7.4). The diluted sample is then placed in a heating block and warmed to 35-40° C. under a filtered stream of nitrogen or air. As the ethanol evaporates, AmB precipitates. The phosphate salt will also precipitate if its concentration is too high in the initial sample (i.e., 70% ethanol). The precipitated AmB is collected by centrifugation and washed twice in 18 mOhm water by resuspension and centrifugation. The final pellet is resuspended in methanol and a 50-100 μL aliquot is removed for later analysis by analytical HPLC. At this point, most of the AmB is a suspension and not a solution. The intent is to remove residual water. The aliquot removed for analytical HPLC is centrifuged, the supernatant is subsequently removed, and the pellet stored at −20° C. The remaining suspension of AmB is transferred to an amber class vial, and the methanol is evaporated. If the vial is weighed beforehand, a net weight of the isolated AmB can be obtained. Then, the sample is capped and stored at 0-4° C.

Products of this example included AmBHP formulations that include, in terms of polyene content, 97% AmB compound.

Analysis of AmB fractions to quantify AmB compound has been consistently performed by reverse phase HPLC, but with several modifications. These modifications include the use of C18 columns of different dimensions and solvents of different compositions. Importantly, they affect retention time and not apparent purity of a given sample.

At least three methods for analysis of AmBHP of the present invention. Method 1 uses a 8×100 mm NovaPak C18, 4 micron; 75:25 methanol:water (vol:vol); isocratic elution, 0.8 mL/min; absorbance monitored at 405 nm; AmBHP dissolved in DMSO; 20 μL injection; retention time of AmBHP ~6 minutes. The second method 2 is similar to the first, but 65:35 methanol:water, and AmBHP retention time increases to approximately 10 minutes. The third method is similar to the others, but 70:30 methanol:water; isocratic, 1.2 mL/min; 8×200 C18 Novapak; and retention time ~10 minutes.

Figure 15:
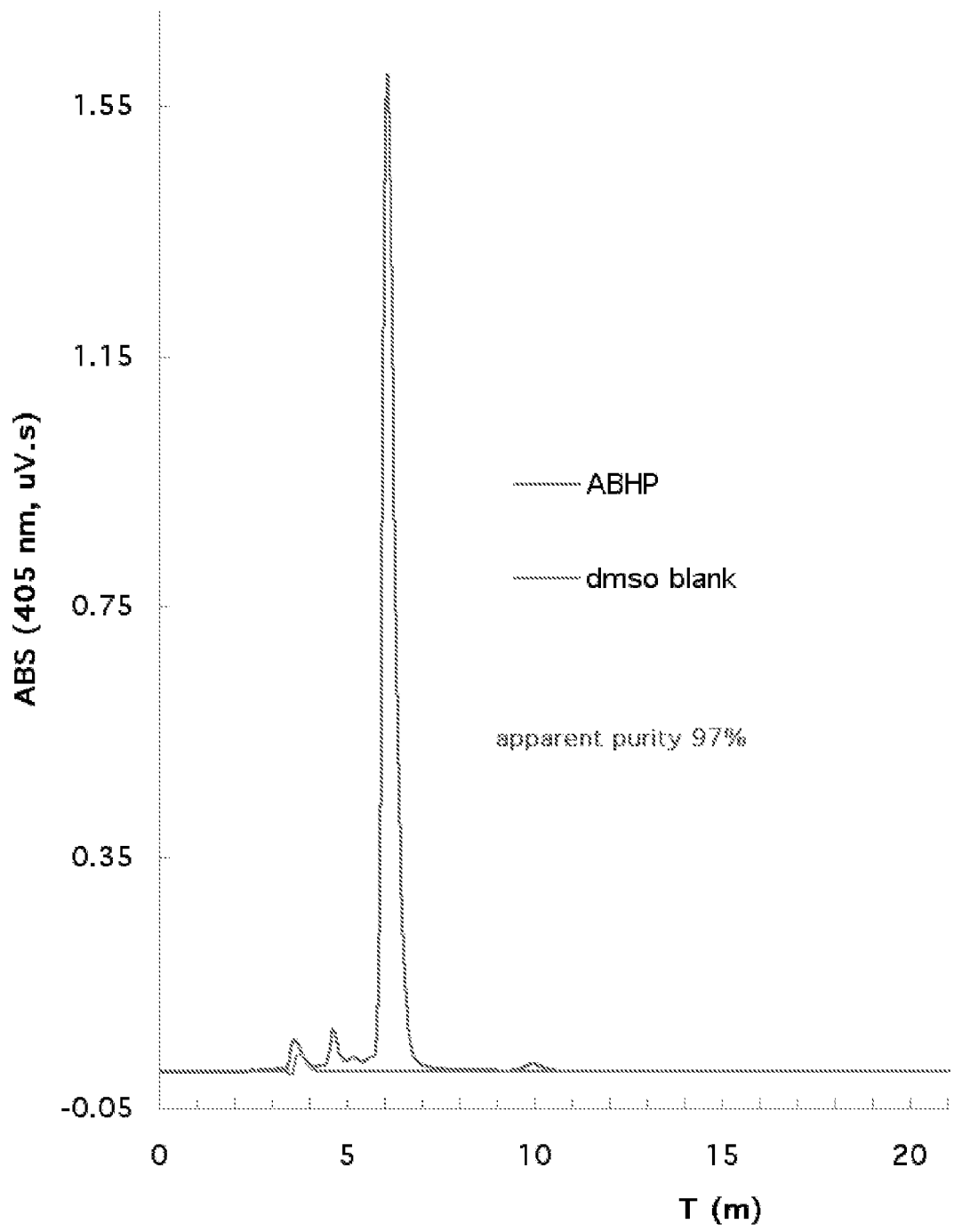
FIG. 15 is an analytical chromatogram of an embodiment of the present invention.

See FIG. 15, an analytical chromatogram of AmBHP as per Method 1.

Example 4

This Example provides a variation of Example 3, and results in AmBHP with apparent purity equal to or greater than 95%.

More specifically, this example was evaluated with a C18 HydroSynergi column with the intent of reducing the amount of AmB that remained on the column and concomitantly, increasing the yield by eluting a greater fraction.

In this Example, the column was a Phenomenex axial pack 21.2×250 mm CN; 10 micron particles; 100 angstrom pore size (washed with ethanol:1 N HCl (99:1; vol:vol) and then equilibrated with running buffer). The solvent is 75:25:0.1 ethanol:water:1 N HCl (vol:vol:vol) (pH of 0.001 N HCl in water ~3). The flow is 0.6 mL/min from 0-85 minutes; linear increase to 3.0 mL/min by 87 minutes; and 3.0 mL/min until 300 minutes. Fractions were collected at 5 minute intervals; fraction volume between 1 and 85 minutes is 5 mL, whereas it is 15 mL after 300 minutes. The absorbance of column effluent is monitored at 363 nm. That measurement is coupled with measurement of the absorbance of an aliquot of each fraction at 405 nm if peaks can not be visualized.

The AmB was USP grade. In this example, about 164 mg USP-AmB were dissolved in 4 mL DMSO, and 600 μL (~25 mg) was injected in each of a series of consecutive runs, with the results of two runs illustrated.

Figure 16:
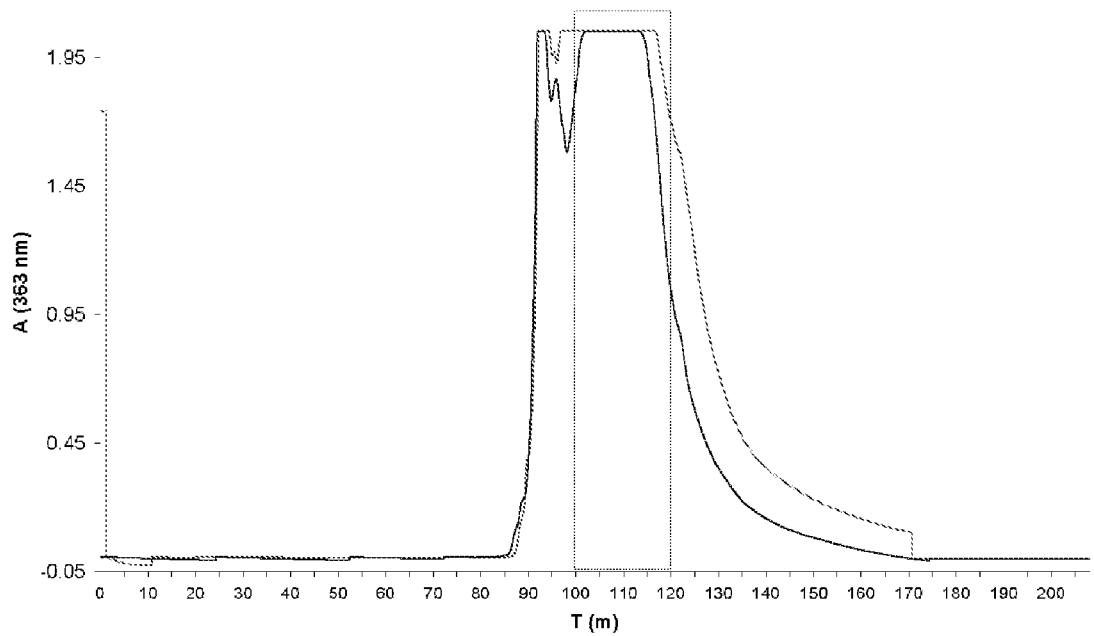
FIG. 16 is a chromatogram showing absorbance at 363 nm.

See FIG. 16, which shows chromatograms of 2 consecutive runs using this variation (absorbance monitored at 363 nm). The clear rectangle indicates the portion of column effluent that was collected as AmBHP.

Post-column work-up of the AmBHP obtained with this variation of CN preparative HPLC was the same as that described above, except that a volume of 20 mM disodium phosphate (pH 7.2) equal to the volume of the pooled fractions was used for dilution of the sample. Then, the pH of the solution was estimated using pH indicator paper, and additional buffer was added until the pH was near neutral. These precautions were necessary to prevent degradation of isolated AmBHP during evaporation of the organic solvent or later during the wash procedure. Other steps were as noted above. The AmBHP obtained by this method, using Analytical Method 1, described above, contained 96% AmB compound.

This example shows a second modification that has resulted in isolation of AmBHP with an apparent purity in the range of 96-98% (based on absorbance at 405 nm and Analytical Method 1, described above), and involves isocratic elution with 90% ethanol:9.99% water:0.01% 1 N HCl (vol:vol:vol) at a flow rate of 5 mL/min. (if in water, pH ~4).

Figure 17:
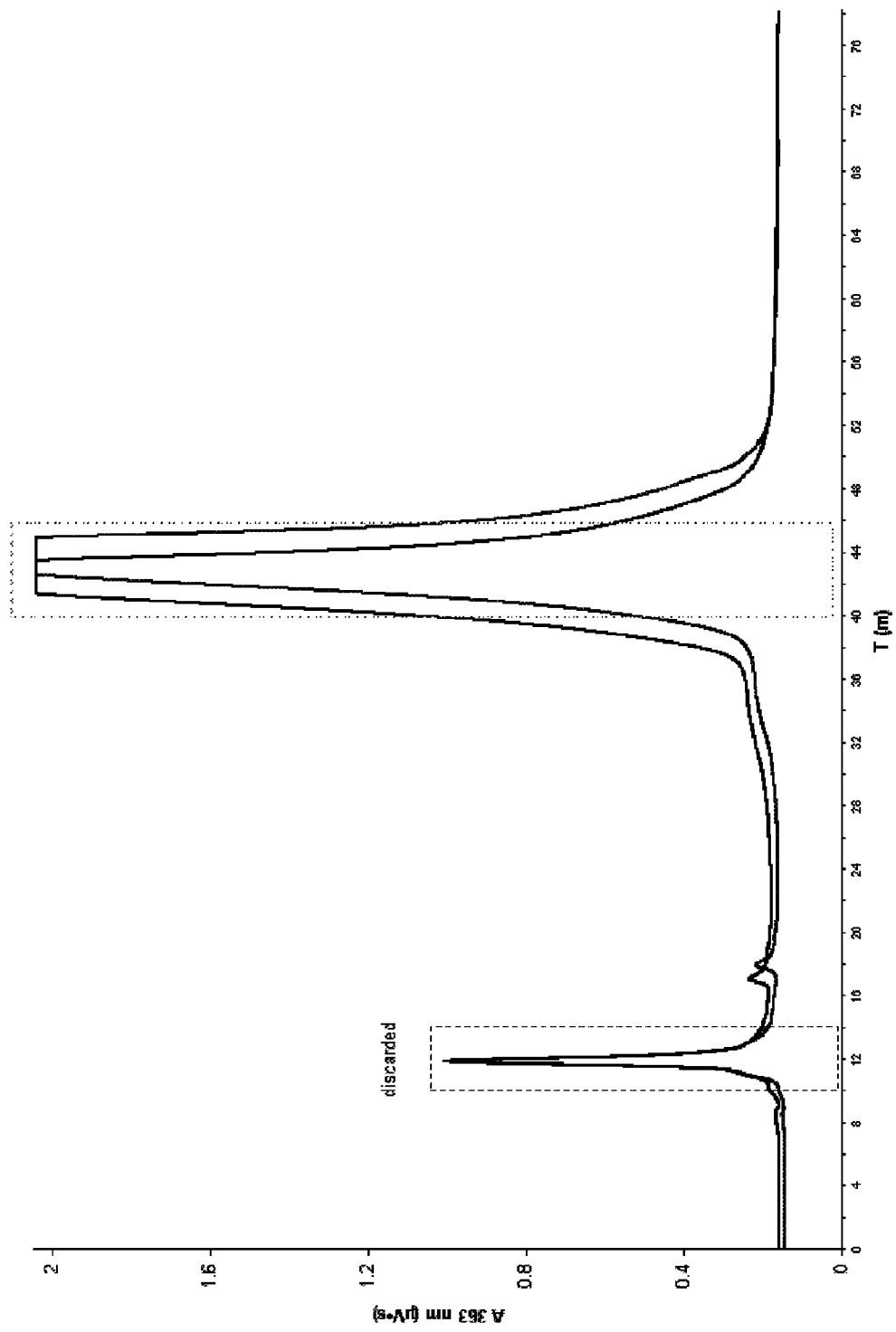
FIG. 17 shows reverse phase HPLC using and AquaC18 column as described in the present invention.

FIG. 17 displays two consecutive chromatograms obtained from injection of 6 mg USP AmB. The peaks enclosed in the dotted rectangle were collected as AmBHP. The apparent purity of the AmBHP isolated in this example was subsequently determined by reverse phase analytical HPLC using an AquaC18 column (as previously described).

The above examples show that a variety of different HPLC methods can be used to obtain AmBHP of the present invention that has an apparent purity equal to or greater than 95%. Additionally, examples where acidification of the elution buffer is used appears to increase the relative solubility of AmB with two potentially important consequences: (a) prevention of concentrated solutions of AmB in DMSO from precipitating in the injector and/or column, and (b) increased yield, more of the AmB is eluted (i.e., less AmB is retained on the column) The latter is taken advantage of by using 99% ethanol:1% 1N HCl (vol:vol) to wash the column and remove AmB that does not elute and eventually interferes with resolution.

As a further embodiment, deoxycholate is also used to solubilize AmBHP.

Example 5

This example shows additional HPLC methods to obtain AmBHP of the present invention. In this example, isolation using a preparative HydroSynergi C18 column (HS-C18; Phenomenex) was evaluated based on the success of the other HPLC methods described herein using an AquaC18 (Phenomenex) to obtain AmBHP for which both the apparent composition and purity were substantially improved over the AmB from which it was isolated.

The preparative column was a 30 mm×250 mm Hydro-Synergi C18 (HS-C18;Phenomenex), 10 micro. Ambient temperature was used for column, sample and solvent. Detection and post column work up of the AmBHP fractions were as described above. Fraction size was determined by flow rate, with 15 mL as the maximal volume for a single fraction and the total volume collected as AmBHP varying between 30-200 mL. The input was USP AmB. For this example, a variety of approaches were evaluated using the HS-C18 preparative column. Some of these approaches were similar to those described for CN HPLC. For example, solubilization of USP AmB in DMSO for loading (with loading volumes equal to or less than 2 mL), and then elution isocratically with varying concentrations of ethanol or methanol in the presence or absence of 0.01-0.0001 N HCl. In addition, gradients of flow rate, solvent concentration or pH were evaluated.

USP AmB was also dissolved in various elution buffers (for example, 70:30 methanol:5 mM phosphate; 70:20:10 methanol:buffer:DMF) to avoid precipitation and increase resolution; loading volumes varied from 2 to 10 mL. Chromatography runs varied from 75-300 minutes to achieve best resolution on the basis of injection volume and elution solvent. The resultant AmBHP contained 92-94% AmB compound The normal phase (silica) HPLC was a 8×100 mm column. There was no retention, no separation from solvent front (DMSO).

The strong anion exchange HPLC was a 8×100 mm column. There was little retention, no resolution of individual components and little resolution from the solvent front (DMSO).

It was found that pH affects solubility and stability of AmB/AmBHP. Additionally, exposure of AmBHP to variations in pH between ~2 and ~11, at least in the short-term, does not appear to adversely affect AmB. As a point in fact, AmBHP can be obtained with elution in ethanol containing 1% 1 N HCL (0.01 N HCl in water has a pH ~2) if the pH during post-column work up is maintained between 5-7. Nor is the apparent purity of AmBHP adversely affected by a short exposure to pH ~11, as occurs during solubilization with deoxycholate. However, at both extremes, AmBHP may degrade during evaporation of solvent under air/nitrogen or during lyophilization. Additionally, during post-column work up, AmBHP may degrade at high temperature. During evaporation of solvent, the temperature of the heating block remained at about 40° C. or less. The presence of DMSO or DMF during drying/lyophilization or prolonged storage (even at −20° C.) may result in degradation.

Thus, in this example, both AmB and AmBHP appear to be stable on the column and during post-column work up if pH and temperature are appropriately controlled and the DMSO or DMF in which it was initially dissolved is removed during chromatography.

The AmBHP of these examples was stored dry, cold (0-4° C.) and dark (amber glass vial).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless specifically otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contains certain errors necessarily resulting from the standard deviation found in their respective testing measurements.

Throughout this application, various publications are referenced, specifically including those listed below. All such references are incorporated herein by reference.

Brajtburg, J., W. G. Powderly, G. S. Kobayashi and G. Medoff. 1990. Amphotericin B: current understanding of mechanisms of action. Antimicrob Agents Chemother. 34:183-188.

Cagnoni, P. J., T. J. Walsh, M. M. Prendergast, D. Bodensteiner, S. Hiemenz, R. N. Greenberg, C. A. Arndt, M. Schuster, N. Seibel, V. Yeldandi, and K. B. Tong. 2000. Pharmacoeconomic analysis of liposomal amphotericin B versus conventional amphotericin B in the empirical treatment of persistently febrile neutropenic patients. J. Clin. Oncol. 18(12):2476-83.

Chavanet, P., V. Joly, D. Rigaud, J. Bolard, C. Carbon, P. Yeni. Influence of diet on experimental toxicity of amphotericin B deoxycholate. Antimicrob. Agents Chemother. 1994; 38(5):963-8.

Cleary, J. D., R. L. Nolan, and S. W. Chapman. 1992 Inhibition of interleukin 1 release from endotoxin or amphotericin B stimulated monocytes. Antimicrob. Agents Chemother. 36(5): 977-981.

Gellai, M., and H. Valtin. 1979. Chronic vascular constrictions and measurements of renal function in conscious rats. Kidney Int. 15(4):419-26.

Goodwin, S. D., J. D. Cleary, C. A. Walawander, J. W. Taylor, T. H. Grasela. 1995. Pretreatment regimens for adverse events related to infusion of amphotericin B. Clin. Infect. Dis. 20(4):755-61.

Grynkiewicz, G., M. Poenie, and R. Y. Tsien. 1985. A new generation of Ca2+ indicators with greatly improved fluorescence properties. J. Biol. Chem. 260: 3440-3450.

Gudlaugsson O., S. Gillespie, K. Lee, J. Van de Berg, J. Hu, S. Messer, L. Herwaldt, M. Pfaller, and D. Diekema. 2003. Attributable mortality of nosocomial candidemia, revisited. Clin. Infect. Dis. 37: 1172-1177.

Harbarth, S., J. P. Burke, J. F. Lloyd, R. S. Evans, S. L. Pestotnik, and M. H. Samore. 2002. Clinical and economic outcomes of conventional amphotericin B-associated nephrotoxicity. Clin. Infect. Dis. 35(12):e120-7.

Kramer, R. E. 1990. Evidence that angiotensin II decreases mitochondrial calcium in the glomerulosa cell. Molec. Cell Endocrinol. 74:87-100.

Kramer, R. E. 1988. Angiotensin II-stimulated changes in calcium metabolism in cultured bovine glomerulosa cells. Molec. Cell Endocrinol. 60:199-210.

Kramer, R. E. 1988. Angiotensin II causes sustained elevations of cytosolic calcium in glomerulosa cells. Amer. J. Physiol. 255:E338.

Lewis, J S, Boucher H W, Lubowski T J, Ambegaonkar A J, Day D L, and Patterson T F. 2005. Cost advantage of voriconazole over amphotericin B deoxycholate for primary treatment of invasive aspergillosis. Pharmacotherapy. 25(6):839-46.

Liao, R. S., R. P. Rennie and J. A. Talbot. 1999. Assessment of the effect of amphotericin B on the vitality of *Candida albicans*. Antimicrob. Agents Chemother. 43:1034-1041.

Luber, A. D., L. Maa, M. Lam, and B. J. Guglielmo. 1999. Risk factors for AmB-induced nephrotoxicity. J. Antimicrob. Chemother. 43:267-271.

Mitsutake, K., S. Kohno, Y. Miyazaki, T. Noda, H. Miyazaki, T. Miyazaki, M. Kaku, H. Koga, and K. Hara. 1994. In vitro and in vivo antifungal activities of liposomal amphotericin B, and amphotericin B lipid complex. Mycopathologia. 128(1):13-7.

NCCLS, Reference Method for Broth Dilution Antifungal Susceptibility Testing of Yeasts; Approved Standard M27-A. National Committee on Clinical Laboratory Standards, 1997. 17(9).

Novak, J., J. Reckelhoff, L. Bumgarner, K. Cockrell, S. Kassamb, and Granger J. P. 1997. Reduced sensitivity of the renal circulation to angiotensin II in pregnant rats. Hypertension. 30:580-4.

Ostrosky-Zeichner, L., K. A. Marr, J. H. Rex, and S. H. Cohen. 2003. Amphotericin B: Time for a new "Gold Standard". Clin. Infect. Dis. 37; 415-25.

Ramos, H., E. Valdivieso, M. Gamargo, F. Dagger and B. E. Cohen. 1996. Amphotericin B kills unicellular *Leishmania* by forming aqueous pores permeable to small cations and anions. J. Membrane Biol. 152:65-75.

Rogers, P. D., J. K. Jenkins, S. W. Chapman, K. Ndebele, B. A. Chapman, and J. D. Cleary. 1998. Amphotericin B activation of human genes encoding for cytokines. J. Inf. Dis. 178: 1726-33.

Rogers, P D, R. E. Kramer, S. W. Chapman, and J. D. Cleary. 1999. Calcium-mediated signal transduction of amphotericin B-induced interleukin-1β expression in human monocytic cells. J. Inf. Dis. 180: 1259-1266.

Sabra, R., and R. A. Branch. 1992. Effect of amphotericin B on intracellular calcium levels in cultured glomerular mesangial cells. Eur. J. Pharmacol. 226:79-85.

Walsh, T. J., J. W. Hiemenz, N. L. Seibel, J. R. Perfect, G. Horwith, L. Lee, J. L. Silber, M. J. DiNubile, A. Reboli, E. Bow, J. Lister, and E. J. Anaissie. 1998. AmB lipid complex for invasive fungal infections: Analysis of safety and efficacy in 556 cases. Clin. Infect. Dis. 26:1383-96.

Wey, S. B., M. Mori, M. A. Pfaller, R. F. Woolson, and R. P. Wenzel. 1989. Risk factors for hospital-acquired candidemia. A matched case-control study. Arch. Intern. Med. 149: 2349-2353.

White, M. H., R. A. Bowden, E. S. Sandler, M. L. Graham, G. A. Noskin, J. R. Wingard, M. Goldman, J. A. van Burik, A. McCabe, J. S. Lin, M. Gurwith, and C. B. Miller. 1998. Randomized, double-blind clinical trial of AmB colloidal dispersion vs. AmB in the empirical treatment of fever and neutropenia. Clin. Infect. Dis. 27:296-302.

Wingard, J. R., P. Kubilis, L. Lee, G. Yee, M. White, L. Walshe, R. Bowden, E. Anaissie, J. Hiemenz, and J. Lister. 1999. Clinical significance of nephrotoxicity in patients treated with AmB for suspected or proven aspergillosis. Clin. Infect. Dis. 29:1402-1407.

Wingard, J. R., M. H. White, E. Anaissie, J. Raffalli, J. Goodman, A. Arrieta, and LAmph/ABLC Collaborative Study Group. 2000. A randomized, double-blind comparative trial evaluating the safety of liposomal AmB versus AmB lipid complex in the empirical treatment of febrile neutropenia. Clin. Infect. Dis. 31:1155-6.

We claim:

1. A method of ameliorating amphotericin treatment side effects, comprising:
providing a formulation that comprises a polyene active ingredient that includes amphotericin B, wherein the amphotericin B compound is present, in terms of polyene content, in an amount greater than 90%, and non-amphotericin B polyene compounds are present in an amount of no greater than 10%, and a pharmaceutically effective carrier; and
administering a therapeutically effective amount of said formulation to a subject in need thereof.

2. The method of claim 1, wherein the amphotericin B compound is present in an amount greater than about 91% and no greater than 9% of non-amphotericin B polyene compounds.

3. The method of claim 1, wherein the amphotericin B compound is present in an amount greater than about 92% and no greater than 8% of non-amphotericin B polyene compounds.

4. The method of claim 1, wherein the amphotericin B compound is present in an amount greater than about 93% and no greater than 7% of non-amphotericin B polyene compounds.

5. The method of claim 1, wherein the amphotericin B compound is present in an amount greater than about 94% and no greater than 6% of non-amphotericin B polyene compounds.

6. The method of claim 1, wherein the amphotericin B compound is present in an amount greater than about 95% and no greater than 5% of non-amphotericin B polyene compounds.

7. The method of claim 1, wherein said pharmaceutically acceptable carrier is a lipid carrier.

8. The method of claim 1, wherein the administering step is intravenous.

9. The method of claim 1, wherein the subject is in need of treatment for a fungal infection.

10. A pharmaceutical composition, comprising:
a polyene active ingredient that includes amphotericin B, wherein the amphotericin B compound is present, in terms of polyene content, in an amount greater than 90%, and non-amphotericin B polyene compounds are present in an amount of no greater than 10%, and a pharmaceutically effective carrier.

11. The composition of claim 10, wherein the amphotericin B compound is present in an amount greater than about 91% and no greater than 9% of non-amphotericin B polyene compounds.

12. The composition of claim 10, wherein the amphotericin B compound is present in an amount greater than about 92% and no greater than 8% of non-amphotericin B polyene compounds.

13. The composition of claim 10, wherein the amphotericin B compound is present in an amount greater than about 93% and no greater than 7% of non-amphotericin B polyene compounds.

14. The composition of claim 10, wherein the amphotericin B compound is present in an amount greater than about 94% and no greater than 6% of non-amphotericin B polyene compounds.

15. The composition of claim 10, wherein the amphotericin B compound is present in an amount greater than about 95% and no greater than 5% of non-amphotericin B polyene compounds.

16. A pharmaceutical composition that comprises:
a polyene active ingredient that has at least 90% w/w of a compound of the following formula:

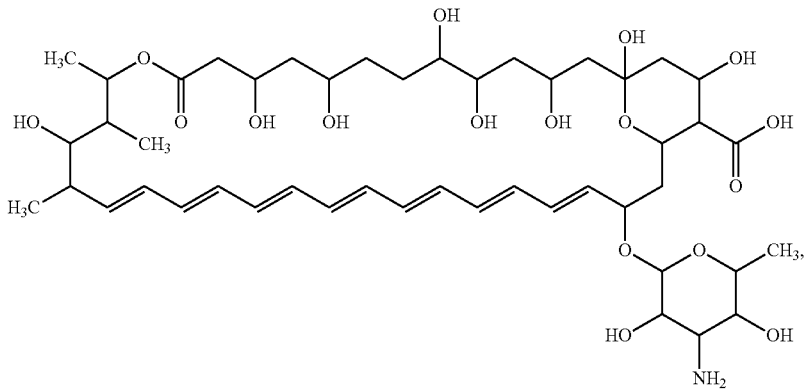 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 10% w/w of at least one of a non-amphotericin B polyene compound,
and a pharmaceutically acceptable carrier.

17. The composition of claim 16, wherein the polyene active ingredient comprises at least 91% w/w of a compound of the following formula:

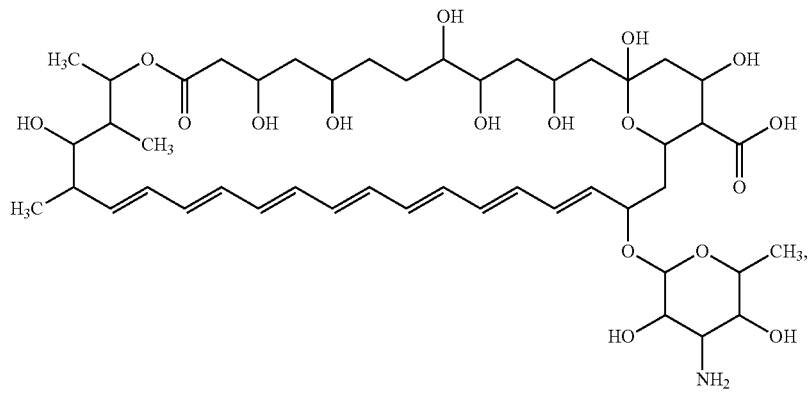 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 9% w/w of at least one of a non-amphotericin B polyene compound.

18. The composition of claim 16, wherein the polyene active ingredient comprises at least 92% w/w of a compound of the following formula:

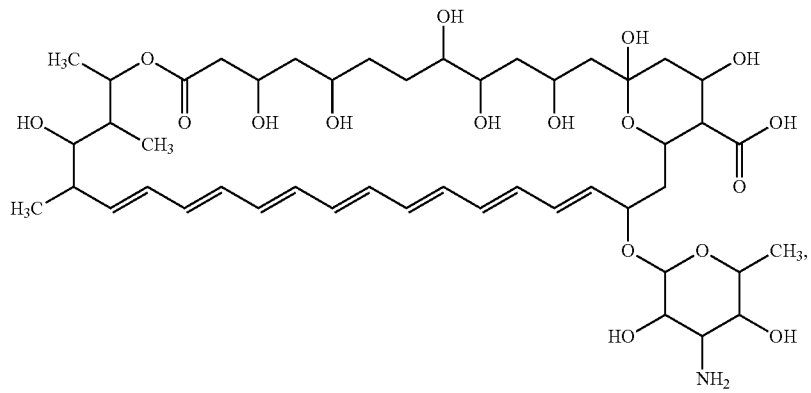 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 8% w/w of at least one of a non-amphotericin B polyene compound.

19. The composition of claim 16, wherein the polyene active ingredient comprises at least 93% w/w of a compound of the following formula:

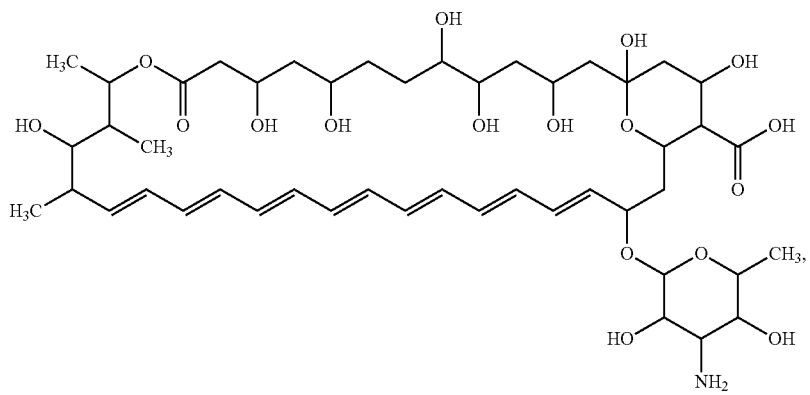 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 7% w/w of at least one of a non-amphotericin B polyene compound.

20. The composition of claim 16, wherein the polyene active ingredient comprises at least 94% w/w of a compound of the following formula:

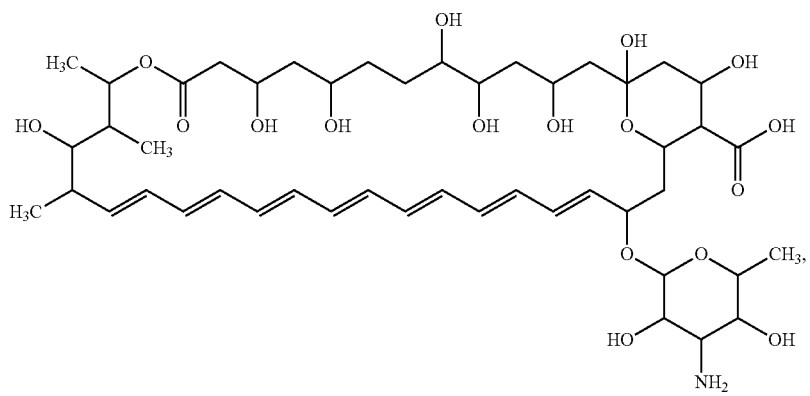 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 6% w/w of at least one of a non-amphotericin B polyene compound.

21. The composition of claim 16, wherein the polyene active ingredient comprises at least 95% w/w of a compound of the following formula:

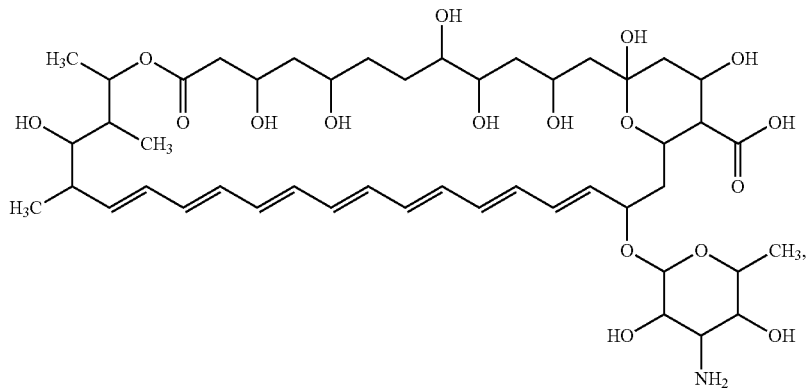 [SMILES: CC1/C=C/C=C/C=C/C=C/C=C/C=C/C=C/C(OC2OC(C)C(O)C(N)C2O)CC2OC(O)(CC(O)CC(O)C(O)CCC(O)CC(O)CC(=O)OC(C)C(C)C1O)CC(O)C2C(=O)O]

and comprises no greater 5% w/w of at least one of a non-amphotericin B polyene compound.

22. A method of making an amphotericin B composition, comprising:
provide USP compliant amphotericin B;
introducing the amphotericin B into a liquid chromatography column;
isolating a polyene solute that comprises, in terms of polyene content, a compound of the following formula:

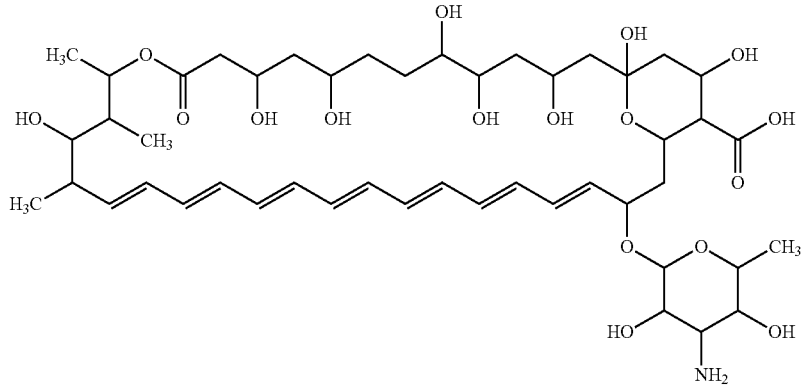

in an amount greater than 90%, and non-amphotericin B polyene compounds are present in an amount of no greater than 10%,
collecting the solute and combining the solute with a pharmaceutically acceptable carrier.

23. The method of claim 20, wherein the solute comprises the following formula:

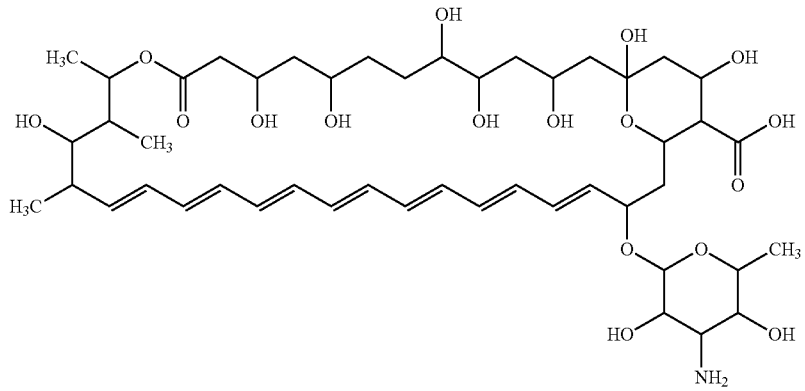

in an amount greater than 91%, and non-amphotericin B polyene compounds are present in an amount of no greater than 9%.

24. The method of claim 20, wherein the solute comprises the following formula:

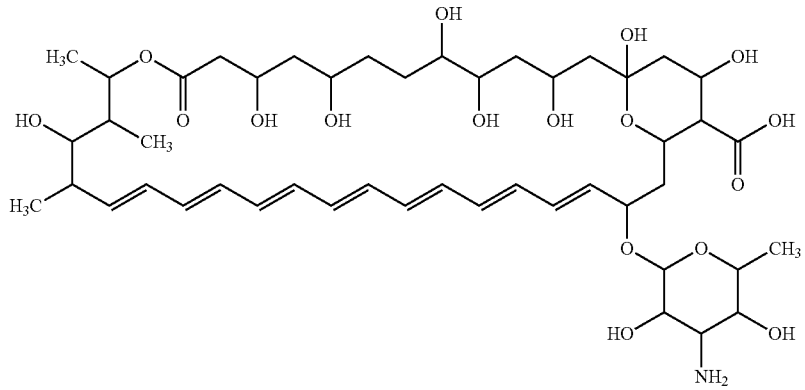

in an amount greater than 92%, and non-amphotericin B polyene compounds are present in an amount of no greater than 8%.

25. The method of claim 20, wherein the solute comprises the following formula:

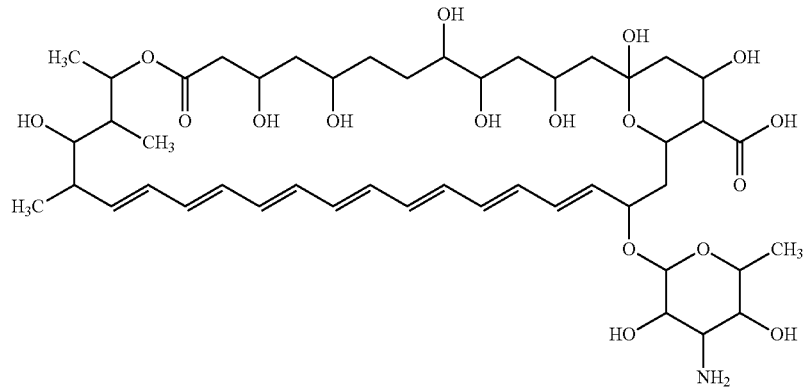

in an amount greater than 93%, and non-amphotericin B polyene compounds are present in an amount of no greater than 7%.

26. The method of claim 20, wherein the solute comprises the following formula:

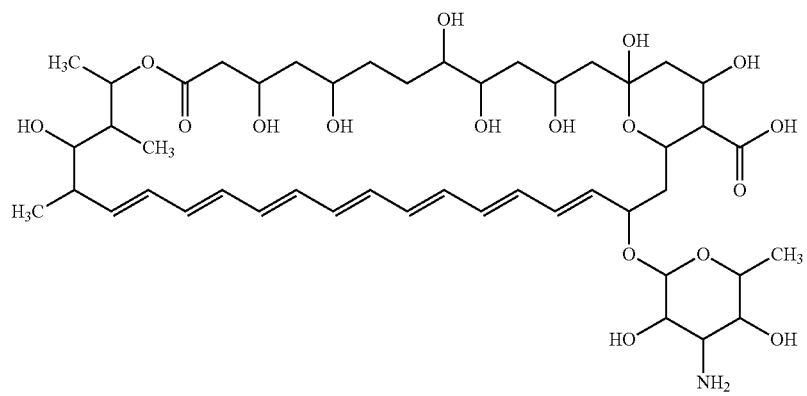

in an amount greater than 94%, and non-amphotericin B polyene compounds are present in an amount of no greater than 6%.

27. The method of claim 20, wherein the solute comprises the following formula:

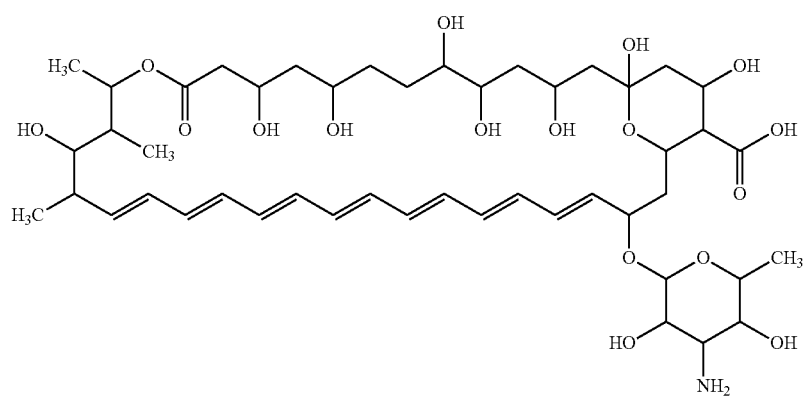

in an amount greater than 95%, and non-amphotericin B polyene compounds are present in an amount of no greater than 5%.

28. The method of claim 20, wherein the liquid chromatography is high pressure liquid chromatography (HPLC).

29. The method of claim 20, wherein the column comprises a gradient of methanol and sodium phosphate.

30. The method of claim 26, wherein the column flow rate is about 1.5 mL/min.

* * * * *